US011839766B2

(12) United States Patent
Scheltienne et al.

(10) Patent No.: US 11,839,766 B2
(45) Date of Patent: Dec. 12, 2023

(54) NEUROMODULATION SYSTEM

(71) Applicant: ONWARD MEDICAL N.V., Eindhoven (NL)

(72) Inventors: Mathieu Scheltienne, Eindhoven (NL); Edoardo Paoles, Eindhoven (NL); Jeroen Tol, Eindhoven (NL); Jurriaan Bakker, Eindhoven (NL)

(73) Assignee: Onward Medical N.V., Eindhoven (NL)

( * ) Notice: Subject to any disclaimer, the term of this patent is extended or adjusted under 35 U.S.C. 154(b) by 29 days.

(21) Appl. No.: 17/098,183

(22) Filed: Nov. 13, 2020

(65) Prior Publication Data
US 2021/0154475 A1 May 27, 2021

(30) Foreign Application Priority Data

Nov. 27, 2019 (EP) ..................................... 19211698

(51) Int. Cl.
*A61N 1/36* (2006.01)
*A61N 1/05* (2006.01)
(Continued)

(52) U.S. Cl.
CPC .......... *A61N 1/36062* (2017.08); *A61B 34/10* (2016.02); *A61N 1/0551* (2013.01);
(Continued)

(58) Field of Classification Search
CPC .......................... A61N 1/0551; A61N 1/36062
See application file for complete search history.

(56) References Cited

U.S. PATENT DOCUMENTS 2,868,343 A 1/1959 Sproul
3,543,761 A 12/1970 Bradley
(Continued)

FOREIGN PATENT DOCUMENTS

AU 2012204526 9/2016
CA 2856202 A1 5/2013
(Continued)

OTHER PUBLICATIONS

Sharrad, W., "The Segmental Innervation of the Lower Limb Muscles in Man," Annals Royal College of Surgeons of England, vol. 35, No. 2, Jan. 2, 1964, 17 pages.
(Continued)

*Primary Examiner* — Alyssa M Alter
(74) *Attorney, Agent, or Firm* — Finnegan, Henderson, Farabow, Garrett & Dunner, LLP

(57) ABSTRACT

A neuromodulation system comprising:
  at least one input means for inputting patient data into the neuromodulation system;
  at least one model calculation and building means for building a patient model, the patient model describing the anatomy and/or physiology and/or pathophysiology and the real and/or simulated reaction of the patient on a provided and/or simulated neuromodulation;
  at least one computation means for using the patient model (M) and calculating the impact of the provided and/or simulated neuromodulation.
The present invention further relates to a method for providing neuromodulation.

19 Claims, 6 Drawing Sheets

(51) Int. Cl.
  *A61B 34/10* (2016.01)
  *G16H 20/40* (2018.01)
  *G16H 30/20* (2018.01)
  *A61B 90/00* (2016.01)
  *A61B 17/00* (2006.01)

(52) U.S. Cl.
  CPC ..... *A61N 1/36067* (2013.01); *A61N 1/36175* (2013.01); *G16H 20/40* (2018.01); *G16H 30/20* (2018.01); *A61B 2017/00039* (2013.01); *A61B 2017/00044* (2013.01); *A61B 2034/104* (2016.02); *A61B 2034/105* (2016.02); *A61B 2034/107* (2016.02); *A61B 2090/373* (2016.02); *A61B 2090/374* (2016.02); *A61B 2090/3762* (2016.02); *A61N 1/36103* (2013.01)

(56) References Cited

U.S. PATENT DOCUMENTS

| | | |
|---|---|---|
| 3,650,277 A | 3/1972 | Sjostrand et al. |
| 3,662,758 A | 5/1972 | Glover |
| 3,724,467 A | 4/1973 | Avery et al. |
| 4,044,774 A | 8/1977 | Corbin et al. |
| 4,102,344 A | 7/1978 | Conway et al. |
| 4,141,365 A | 2/1979 | Fischell et al. |
| 4,285,347 A | 8/1981 | Hess |
| 4,340,063 A | 7/1982 | Maurer |
| 4,379,462 A | 4/1983 | Borkan et al. |
| 4,398,537 A | 8/1983 | Holmbo |
| 4,414,986 A | 11/1983 | Dickhudt et al. |
| 4,538,624 A | 9/1985 | Tarjan |
| 4,549,556 A | 10/1985 | Tarjan et al. |
| 4,559,948 A | 12/1985 | Liss et al. |
| 4,569,352 A | 2/1986 | Petrofsky et al. |
| 4,573,481 A | 3/1986 | Bullara |
| 4,724,842 A | 2/1988 | Charters |
| 4,800,898 A | 1/1989 | Hess et al. |
| 4,934,368 A | 6/1990 | Lynch |
| 4,969,452 A | 11/1990 | Petrofsky et al. |
| 5,002,053 A | 3/1991 | Garcia-Rill et al. |
| 5,031,618 A | 7/1991 | Mullet |
| 5,066,272 A | 11/1991 | Eaton et al. |
| 5,081,989 A | 1/1992 | Graupe et al. |
| 5,121,754 A | 6/1992 | Mullett |
| 5,344,439 A | 9/1994 | Otten |
| 5,354,320 A | 10/1994 | Schaldach et al. |
| 5,366,813 A | 11/1994 | Berlin |
| 5,374,285 A | 12/1994 | Vaiani et al. |
| 5,417,719 A | 5/1995 | Hull et al. |
| 5,476,441 A | 12/1995 | Durfee et al. |
| 5,562,718 A | 10/1996 | Palermo |
| 5,643,330 A | 7/1997 | Holsheimer et al. |
| 5,733,322 A | 3/1998 | Starkebaum |
| 5,983,141 A | 11/1999 | Sluijter et al. |
| 6,058,331 A | 5/2000 | King |
| 6,066,163 A | 5/2000 | John |
| 6,104,957 A | 8/2000 | Alo et al. |
| 6,122,548 A | 9/2000 | Starkebaum et al. |
| 6,308,103 B1 | 10/2001 | Gielen |
| 6,319,241 B1 | 11/2001 | King et al. |
| 6,463,327 B1 | 10/2002 | Lurie et al. |
| 6,470,213 B1 | 10/2002 | Alley |
| 6,500,110 B1 | 12/2002 | Davey et al. |
| 6,503,231 B1 | 1/2003 | Prausnitz et al. |
| 6,505,074 B2 | 1/2003 | Boveja et al. |
| 6,516,227 B1 | 2/2003 | Meadows et al. |
| 6,551,849 B1 | 4/2003 | Kenney |
| 6,587,724 B2 | 7/2003 | Mann |
| 6,662,053 B2 | 12/2003 | Borkan |
| 6,666,831 B1 | 12/2003 | Edgerton et al. |
| 6,685,729 B2 | 2/2004 | Gonzalez |
| 6,748,276 B1 | 6/2004 | Daignault, Jr. et al. |
| 6,819,956 B2 | 11/2004 | DiLorenzo |
| 6,839,594 B2 | 1/2005 | Cohen et al. |
| 6,862,479 B1 | 3/2005 | Whitehurst et al. |
| 6,871,099 B1 | 3/2005 | Whitehurst et al. |
| 6,878,112 B2 | 4/2005 | Linberg et al. |
| 6,892,098 B2 | 5/2005 | Ayal et al. |
| 6,895,280 B2 | 5/2005 | Meadows et al. |
| 6,895,283 B2 | 5/2005 | Erickson et al. |
| 6,937,891 B2 | 8/2005 | Leinders et al. |
| 6,950,706 B2 | 9/2005 | Rodriguez et al. |
| 6,975,907 B2 | 12/2005 | Zanakis et al. |
| 6,988,006 B2 | 1/2006 | King et al. |
| 6,999,820 B2 | 2/2006 | Jordan |
| 7,020,521 B1 | 3/2006 | Brewer et al. |
| 7,024,247 B2 | 4/2006 | Gliner et al. |
| 7,035,690 B2 | 4/2006 | Goetz |
| 7,047,084 B2 | 5/2006 | Erickson et al. |
| 7,065,408 B2 | 6/2006 | Herman et al. |
| 7,096,070 B1 | 8/2006 | Jenkins et al. |
| 7,110,820 B2 | 9/2006 | Tcheng et al. |
| 7,127,287 B2 | 10/2006 | Duncan et al. |
| 7,127,296 B2 | 10/2006 | Bradley |
| 7,127,297 B2 | 10/2006 | Law et al. |
| 7,149,773 B2 | 12/2006 | Haller et al. |
| 7,153,242 B2 | 12/2006 | Goffer |
| 7,184,837 B2 | 2/2007 | Goetz |
| 7,200,443 B2 | 4/2007 | Faul |
| 7,209,787 B2 | 4/2007 | DiLorenzo |
| 7,228,179 B2 | 6/2007 | Van Campen et al. |
| 7,239,920 B1 | 7/2007 | Thacker et al. |
| 7,251,529 B2 | 7/2007 | Greenwood-Van Meerveld |
| 7,252,090 B2 | 8/2007 | Goetz |
| 7,313,440 B2 | 12/2007 | Miesel |
| 7,324,853 B2 | 1/2008 | Ayal et al. |
| 7,330,760 B2 | 2/2008 | Heruth et al. |
| 7,337,005 B2 | 2/2008 | Kim et al. |
| 7,337,006 B2 | 2/2008 | Kim et al. |
| 7,340,298 B1 | 3/2008 | Barbut |
| 7,377,006 B2 | 5/2008 | Genoa et al. |
| 7,381,192 B2 | 6/2008 | Brodard et al. |
| 7,415,309 B2 | 8/2008 | McIntyre |
| 7,463,927 B1 | 12/2008 | Chaouat |
| 7,463,928 B2 | 12/2008 | Lee et al. |
| 7,467,016 B2 | 12/2008 | Colborn |
| 7,493,170 B1 | 2/2009 | Segel et al. |
| 7,496,404 B2 | 2/2009 | Meadows et al. |
| 7,502,652 B2 | 3/2009 | Gaunt et al. |
| 7,536,226 B2 | 5/2009 | Williams et al. |
| 7,544,185 B2 | 6/2009 | Bengtsson |
| 7,584,000 B2 | 9/2009 | Erickson |
| 7,590,454 B2 | 9/2009 | Garabedian et al. |
| 7,603,178 B2 | 10/2009 | North et al. |
| 7,620,502 B2 | 11/2009 | Selifonov et al. |
| 7,628,750 B2 | 12/2009 | Cohen et al. |
| 7,647,115 B2 | 1/2010 | Levin et al. |
| 7,742,037 B2 | 1/2010 | Sako et al. |
| 7,660,636 B2 | 2/2010 | Castel et al. |
| 7,697,995 B2 | 4/2010 | Cross, Jr. et al. |
| 7,725,193 B1 | 5/2010 | Chu |
| 7,729,781 B2 | 6/2010 | Swoyer et al. |
| 7,734,340 B2 | 6/2010 | de Ridder |
| 7,734,351 B2 | 6/2010 | Testerman et al. |
| 7,769,463 B2 | 8/2010 | Katsnelson |
| 7,797,057 B2 | 9/2010 | Harris |
| 7,801,601 B2 | 9/2010 | Maschino et al. |
| 7,813,803 B2 | 10/2010 | Heruth et al. |
| 7,813,809 B2 | 10/2010 | Strother et al. |
| 7,856,264 B2 | 12/2010 | Firlik et al. |
| 7,877,146 B2 | 1/2011 | Rezai et al. |
| 7,890,182 B2 | 2/2011 | Parramon et al. |
| 7,949,395 B2 | 5/2011 | Kuzma |
| 7,949,403 B2 | 5/2011 | Palermo et al. |
| 7,987,000 B2 | 7/2011 | Moffitt et al. |
| 7,991,465 B2 | 8/2011 | Bartic et al. |
| 8,019,427 B2 | 9/2011 | Moffitt |
| 8,050,773 B2 | 11/2011 | Zhu |
| 8,108,051 B2 | 1/2012 | Cross, Jr. et al. |
| 8,108,052 B2 | 1/2012 | Boling |
| 8,131,358 B2 | 3/2012 | Moffitt et al. |
| 8,135,473 B2 | 3/2012 | Miesel et al. |
| 8,155,750 B2 | 4/2012 | Jaax et al. |
| 8,168,481 B2 | 5/2012 | Hanaoka et al. |

(56) References Cited

U.S. PATENT DOCUMENTS

| | | | |
|---|---|---|---|
| 8,170,660 B2 | 5/2012 | Dacey, Jr. et al. |
| 8,190,262 B2 | 5/2012 | Gerber et al. |
| 8,195,304 B2 | 6/2012 | Strother et al. |
| 8,214,048 B1 | 7/2012 | Whitehurst et al. |
| 8,229,565 B2 | 7/2012 | Kim et al. |
| 8,239,038 B2 | 8/2012 | Wolf, II |
| 8,260,436 B2 | 9/2012 | Gerber et al. |
| 8,271,099 B1 | 9/2012 | Swanson |
| 8,295,936 B2 | 10/2012 | Wahlstrand et al. |
| 8,311,644 B2 | 11/2012 | Moffitt et al. |
| 8,326,569 B2 | 12/2012 | Lee et al. |
| 8,332,029 B2 | 12/2012 | Glukhovsky et al. |
| 8,332,047 B2 | 12/2012 | Libbus et al. |
| 8,346,366 B2 | 1/2013 | Arle et al. |
| 8,352,036 B2 | 1/2013 | DiMarco et al. |
| 8,355,791 B2 | 1/2013 | Moffitt |
| 8,355,797 B2 | 1/2013 | Caparso et al. |
| 8,364,273 B2 | 1/2013 | de Ridder |
| 8,369,961 B2 | 2/2013 | Christman et al. |
| 8,374,696 B2 | 2/2013 | Sanchez et al. |
| 8,412,345 B2 | 4/2013 | Moffitt |
| 8,428,728 B2 | 4/2013 | Sachs |
| 8,442,655 B2 | 5/2013 | Moffitt et al. |
| 8,452,406 B2 | 5/2013 | Arcot-Krishnamurthy et al. |
| 8,543,200 B2 | 9/2013 | Lane et al. |
| 8,588,884 B2 | 11/2013 | Hegde et al. |
| 8,626,300 B2 | 1/2014 | Demarais et al. |
| 8,700,145 B2 | 4/2014 | Kilgard et al. |
| 8,712,546 B2 | 4/2014 | Kim et al. |
| 8,740,825 B2 | 6/2014 | Ehrenreich et al. |
| 8,750,957 B2 | 6/2014 | Tang et al. |
| 8,768,481 B2 | 7/2014 | Lane |
| 8,805,542 B2 | 8/2014 | Tai et al. |
| 9,072,891 B1 | 7/2015 | Rao |
| 9,079,039 B2 | 7/2015 | Carlson et al. |
| 9,101,769 B2 | 8/2015 | Edgerton et al. |
| 9,205,259 B2 | 12/2015 | Kim et al. |
| 9,205,260 B2 | 12/2015 | Kim et al. |
| 9,205,261 B2 | 12/2015 | Kim et al. |
| 9,248,291 B2 | 2/2016 | Mashiach |
| 9,272,139 B2 | 3/2016 | Hamilton et al. |
| 9,272,143 B2 | 3/2016 | Libbus et al. |
| 9,283,391 B2 | 3/2016 | Ahmed |
| 9,314,630 B2 | 4/2016 | Levin et al. |
| 9,393,409 B2 | 7/2016 | Edgerton et al. |
| 9,409,023 B2 | 8/2016 | Burdick et al. |
| 9,415,218 B2 | 8/2016 | Edgerton et al. |
| 9,421,365 B2 | 8/2016 | Sumners et al. |
| 9,597,517 B2 | 3/2017 | Moffitt |
| 9,610,442 B2 | 4/2017 | Yoo et al. |
| 9,802,052 B2 | 10/2017 | Marnfeldt |
| 9,895,545 B2 | 2/2018 | Rao et al. |
| 9,993,642 B2 | 6/2018 | Gerasimenko et al. |
| 10,092,750 B2 | 10/2018 | Edgerton et al. |
| 10,124,166 B2 | 11/2018 | Edgerton et al. |
| 10,137,299 B2 | 11/2018 | Lu et al. |
| 10,406,366 B2 | 9/2019 | Westlund et al. |
| 10,449,371 B2 | 10/2019 | Serrano Carmona |
| 10,751,533 B2 | 8/2020 | Edgerton et al. |
| 10,773,074 B2 | 9/2020 | Liu et al. |
| 10,806,927 B2 | 10/2020 | Edgerton et al. |
| 10,806,935 B2 | 10/2020 | Rao et al. |
| 11,097,122 B2 | 8/2021 | Lu |
| 11,123,312 B2 | 9/2021 | Lu et al. |
| 2001/0016266 A1 | 8/2001 | Okazaki et al. |
| 2001/0032992 A1 | 10/2001 | Wendt |
| 2002/0042814 A1 | 4/2002 | Fukasawa et al. |
| 2002/0052539 A1 | 5/2002 | Haller et al. |
| 2002/0055779 A1 | 5/2002 | Andrews |
| 2002/0083240 A1 | 6/2002 | Hoese et al. |
| 2002/0111661 A1 | 8/2002 | Cross et al. |
| 2002/0115945 A1 | 8/2002 | Herman et al. |
| 2002/0188332 A1 | 12/2002 | Lurie et al. |
| 2002/0193843 A1 | 12/2002 | Hill et al. |
| 2003/0032992 A1 | 2/2003 | Thacker et al. |
| 2003/0078633 A1 | 4/2003 | Firlik et al. |
| 2003/0093021 A1 | 5/2003 | Goffer |
| 2003/0100933 A1 | 5/2003 | Ayal et al. |
| 2003/0114894 A1 | 6/2003 | Dar et al. |
| 2003/0158583 A1 | 8/2003 | Burnett et al. |
| 2003/0200323 A1 | 10/2003 | Dold et al. |
| 2003/0220679 A1 | 11/2003 | Han |
| 2003/0233137 A1 | 12/2003 | Paul, Jr. |
| 2004/0039425 A1 | 2/2004 | Greenwood-Van Meerveld |
| 2004/0044380 A1 | 3/2004 | Bruninga et al. |
| 2004/0111118 A1 | 6/2004 | Hill et al. |
| 2004/0111126 A1 | 6/2004 | Tanagho et al. |
| 2004/0122483 A1 | 6/2004 | Nathan et al. |
| 2004/0127954 A1 | 7/2004 | McDonald, III |
| 2004/0133248 A1 | 7/2004 | Frei et al. |
| 2004/0138518 A1 | 7/2004 | Rise et al. |
| 2004/0172027 A1 | 9/2004 | Speitling et al. |
| 2004/0172097 A1 | 9/2004 | Brodard et al. |
| 2004/0181263 A1 | 9/2004 | Balzer et al. |
| 2004/0267320 A1 | 12/2004 | Taylor et al. |
| 2005/0004622 A1 | 1/2005 | Cullen et al. |
| 2005/0061315 A1 | 3/2005 | Lee et al. |
| 2005/0070982 A1 | 3/2005 | Heruth et al. |
| 2005/0075669 A1 | 4/2005 | King |
| 2005/0075678 A1 | 4/2005 | Faul |
| 2005/0090756 A1 | 4/2005 | Wolf et al. |
| 2005/0101827 A1 | 5/2005 | Delisle |
| 2005/0102007 A1 | 5/2005 | Ayal et al. |
| 2005/0113882 A1 | 5/2005 | Cameron et al. |
| 2005/0119713 A1 | 6/2005 | Whitehurst et al. |
| 2005/0125045 A1 | 6/2005 | Brighton et al. |
| 2005/0209655 A1 | 9/2005 | Bradley et al. |
| 2005/0231186 A1 | 10/2005 | Saavedra Barrera et al. |
| 2005/0246004 A1 | 11/2005 | Cameron et al. |
| 2005/0277999 A1 | 12/2005 | Strother et al. |
| 2005/0278000 A1 | 12/2005 | Strother et al. |
| 2006/0003090 A1 | 1/2006 | Rodger et al. |
| 2006/0015153 A1 | 1/2006 | Gliner et al. |
| 2006/0018360 A1 | 1/2006 | Tai et al. |
| 2006/0041225 A1 | 2/2006 | Wallace et al. |
| 2006/0041295 A1 | 2/2006 | Osypka |
| 2006/0089696 A1 | 4/2006 | Olsen et al. |
| 2006/0100671 A1 | 5/2006 | Ridder |
| 2006/0111754 A1 | 5/2006 | Rezai et al. |
| 2006/0122678 A1 | 6/2006 | Olsen et al. |
| 2006/0142337 A1 | 6/2006 | Ikeura et al. |
| 2006/0142816 A1 | 6/2006 | Fruitman et al. |
| 2006/0142822 A1 | 6/2006 | Tulgar |
| 2006/0149333 A1 | 7/2006 | Tanagho et al. |
| 2006/0149337 A1 | 7/2006 | John |
| 2006/0189839 A1 | 8/2006 | Laniado et al. |
| 2006/0195153 A1 | 8/2006 | DiUbaldi et al. |
| 2006/0239482 A1 | 10/2006 | Hatoum |
| 2006/0241356 A1 | 10/2006 | Flaherty |
| 2006/0282127 A1 | 12/2006 | Zealear |
| 2007/0004567 A1 | 1/2007 | Shetty et al. |
| 2007/0016097 A1 | 1/2007 | Farquhar et al. |
| 2007/0016266 A1 | 1/2007 | Paul, Jr. |
| 2007/0016329 A1 | 1/2007 | Herr et al. |
| 2007/0021513 A1 | 1/2007 | Agee et al. |
| 2007/0027495 A1 | 2/2007 | Gerber |
| 2007/0047852 A1 | 3/2007 | Sharp et al. |
| 2007/0048814 A1 | 3/2007 | Muccio |
| 2007/0049814 A1 | 3/2007 | Muccio |
| 2007/0055337 A1 | 3/2007 | Tanrisever |
| 2007/0060954 A1 | 3/2007 | Cameron et al. |
| 2007/0060980 A1 | 3/2007 | Strother et al. |
| 2007/0067003 A1 | 3/2007 | Sanchez et al. |
| 2007/0073357 A1 | 3/2007 | Rooney et al. |
| 2007/0083240 A1 | 4/2007 | Peterson et al. |
| 2007/0100389 A1 | 5/2007 | Jaax et al. |
| 2007/0121702 A1 | 5/2007 | LaGuardia et al. |
| 2007/0121709 A1 | 5/2007 | Ittogi |
| 2007/0142874 A1 | 6/2007 | John |
| 2007/0150023 A1 | 6/2007 | Ignagni et al. |
| 2007/0156172 A1 | 7/2007 | Alvarado |
| 2007/0156179 A1 | 7/2007 | S.E. |
| 2007/0156200 A1 | 7/2007 | Kornet et al. |
| 2007/0168008 A1 | 7/2007 | Olsen |

(56) References Cited

U.S. PATENT DOCUMENTS

| | | |
|---|---|---|
| 2007/0179534 A1 | 8/2007 | Firlik et al. |
| 2007/0179579 A1 | 8/2007 | Feler et al. |
| 2007/0191709 A1 | 8/2007 | Swanson |
| 2007/0208381 A1 | 9/2007 | Hill et al. |
| 2007/0233204 A1 | 10/2007 | Lima et al. |
| 2007/0255372 A1 | 11/2007 | Metzler et al. |
| 2007/0265621 A1 | 11/2007 | Matthis et al. |
| 2007/0265679 A1 | 11/2007 | Bradley et al. |
| 2007/0265691 A1 | 11/2007 | Swanson |
| 2007/0276449 A1 | 11/2007 | Gunter et al. |
| 2007/0276450 A1 | 11/2007 | Meadows et al. |
| 2007/0293910 A1 | 12/2007 | Strother et al. |
| 2008/0002227 A1 | 1/2008 | Tsujimoto |
| 2008/0004674 A1 | 1/2008 | King et al. |
| 2008/0009927 A1 | 1/2008 | Vilims |
| 2008/0021513 A1 | 1/2008 | Thacker et al. |
| 2008/0027346 A1 | 1/2008 | Litt et al. |
| 2008/0046049 A1 | 2/2008 | Skubitz et al. |
| 2008/0051851 A1 | 2/2008 | Lin |
| 2008/0071325 A1 | 3/2008 | Bradley |
| 2008/0077192 A1 | 3/2008 | Harry et al. |
| 2008/0103579 A1 | 5/2008 | Gerber |
| 2008/0105185 A1 | 5/2008 | Kuhlman |
| 2008/0140152 A1 | 6/2008 | Imran et al. |
| 2008/0140162 A1 | 6/2008 | Goetz et al. |
| 2008/0140169 A1 | 6/2008 | Imran |
| 2008/0147143 A1 | 6/2008 | Popovic et al. |
| 2008/0154329 A1 | 6/2008 | Pyles et al. |
| 2008/0183224 A1 | 7/2008 | Barolat |
| 2009/0012436 A1 | 1/2009 | Lanfermann et al. |
| 2009/0024997 A1 | 1/2009 | Kobayashi |
| 2009/0093854 A1 | 4/2009 | Leung et al. |
| 2009/0112281 A1 | 4/2009 | Miyazawa et al. |
| 2009/0118365 A1 | 5/2009 | Benson, III et al. |
| 2009/0131995 A1 | 5/2009 | Sloan et al. |
| 2009/0157141 A1 | 6/2009 | Chiao et al. |
| 2009/0198305 A1 | 8/2009 | Naroditsky et al. |
| 2009/0229166 A1 | 9/2009 | Sawrie |
| 2009/0204173 A1 | 10/2009 | Zhao et al. |
| 2009/0270960 A1 | 10/2009 | Zhao et al. |
| 2009/0281529 A1 | 11/2009 | Carriazo |
| 2009/0281599 A1 | 11/2009 | Thacker et al. |
| 2009/0293270 A1 | 12/2009 | Brindley et al. |
| 2009/0299166 A1 | 12/2009 | Nishida et al. |
| 2009/0299167 A1 | 12/2009 | Seymour |
| 2009/0306491 A1 | 12/2009 | Haggers |
| 2010/0004715 A1 | 1/2010 | Fahey |
| 2010/0010646 A1 | 1/2010 | Drew et al. |
| 2010/0023103 A1 | 1/2010 | Elborno |
| 2010/0029040 A1 | 2/2010 | Nomoto |
| 2010/0042193 A1 | 2/2010 | Slavin |
| 2010/0070007 A1 | 3/2010 | Parker et al. |
| 2010/0114205 A1 | 5/2010 | Donofrio et al. |
| 2010/0114239 A1 | 5/2010 | McDonald, III |
| 2010/0125313 A1 | 5/2010 | Lee et al. |
| 2010/0137238 A1 | 6/2010 | Gan et al. |
| 2010/0137938 A1 | 6/2010 | Kishawi et al. |
| 2010/0145428 A1 | 6/2010 | Cameron et al. |
| 2010/0152811 A1 | 6/2010 | Flaherty |
| 2010/0166546 A1 | 7/2010 | Mahan et al. |
| 2010/0168820 A1 | 7/2010 | Maniak et al. |
| 2010/0185253 A1 | 7/2010 | Dimarco et al. |
| 2010/0198298 A1 | 8/2010 | Glukhovsky et al. |
| 2010/0217355 A1 | 8/2010 | Tass et al. |
| 2010/0228310 A1 | 9/2010 | Shuros et al. |
| 2010/0241121 A1 | 9/2010 | Logan et al. |
| 2010/0241191 A1 | 9/2010 | Testerman et al. |
| 2010/0268299 A1 | 10/2010 | Farone |
| 2010/0274312 A1 | 10/2010 | Alataris et al. |
| 2010/0280570 A1 | 11/2010 | Sturm et al. |
| 2010/0305660 A1 | 12/2010 | Hegi et al. |
| 2010/0312304 A1 | 12/2010 | York et al. |
| 2010/0318168 A1 | 12/2010 | Bighetti |
| 2010/0331925 A1 | 12/2010 | Peterson |
| 2011/0006793 A1 | 1/2011 | Peschke et al. |
| 2011/0009919 A1 | 1/2011 | Carbunaru et al. |
| 2011/0016081 A1 | 1/2011 | Basak et al. |
| 2011/0029040 A1 | 2/2011 | Walker et al. |
| 2011/0029044 A1 | 2/2011 | Hyde et al. |
| 2011/0034277 A1 | 2/2011 | Brandes |
| 2011/0034977 A1 | 2/2011 | Janik et al. |
| 2011/0040349 A1 | 2/2011 | Graupe |
| 2011/0054567 A1 | 3/2011 | Lane et al. |
| 2011/0054568 A1 | 3/2011 | Lane et al. |
| 2011/0054570 A1 | 3/2011 | Lane |
| 2011/0054579 A1 | 3/2011 | Kumar et al. |
| 2011/0077660 A1 | 3/2011 | Janik et al. |
| 2011/0082515 A1 | 4/2011 | Libbus et al. |
| 2011/0084489 A1 | 4/2011 | Kaplan |
| 2011/0093043 A1 | 4/2011 | Torgerson et al. |
| 2011/0112601 A1 | 5/2011 | Meadows et al. |
| 2011/0125203 A1 | 5/2011 | Simon et al. |
| 2011/0130804 A1 | 6/2011 | Lin et al. |
| 2011/0152967 A1 | 6/2011 | Simon et al. |
| 2011/0160810 A1 | 6/2011 | Griffith |
| 2011/0166546 A1 | 7/2011 | Jaax et al. |
| 2011/0184482 A1 | 7/2011 | Eberman et al. |
| 2011/0184488 A1 | 7/2011 | De Ridder |
| 2011/0184489 A1 | 7/2011 | Nicolelis et al. |
| 2011/0202107 A1 | 8/2011 | Sunagawa et al. |
| 2011/0208265 A1 | 8/2011 | Erickson et al. |
| 2011/0213266 A1 | 9/2011 | Williams et al. |
| 2011/0218590 A1 | 9/2011 | DeGiorgio et al. |
| 2011/0218594 A1 | 9/2011 | Doron et al. |
| 2011/0224153 A1 | 9/2011 | Levitt et al. |
| 2011/0224665 A1 | 9/2011 | Crosby et al. |
| 2011/0224752 A1 | 9/2011 | Rolston et al. |
| 2011/0224753 A1 | 9/2011 | Palermo et al. |
| 2011/0224757 A1 | 9/2011 | Zdeblick et al. |
| 2011/0230101 A1 | 9/2011 | Tang et al. |
| 2011/0230701 A1 | 9/2011 | Simon et al. |
| 2011/0230702 A1 | 9/2011 | Honour |
| 2011/0231326 A1 | 9/2011 | Marino |
| 2011/0237221 A1 | 9/2011 | Prakash et al. |
| 2011/0237921 A1 | 9/2011 | Askin, III et al. |
| 2011/0245734 A1 | 10/2011 | Wagner et al. |
| 2011/0276107 A1 | 11/2011 | Simon et al. |
| 2011/0288609 A1 | 11/2011 | Tehrani et al. |
| 2011/0295100 A1 | 12/2011 | Hegde et al. |
| 2012/0006793 A1 | 1/2012 | Swanson |
| 2012/0011950 A1 | 1/2012 | Kracke |
| 2012/0013041 A1 | 1/2012 | Cao et al. |
| 2012/0013126 A1 | 1/2012 | Molloy |
| 2012/0016448 A1 | 1/2012 | Lee |
| 2012/0029528 A1 | 2/2012 | MacDonald et al. |
| 2012/0035684 A1 | 2/2012 | Thompson et al. |
| 2012/0041518 A1 | 2/2012 | Kim et al. |
| 2012/0052432 A1 | 3/2012 | Matsuura |
| 2012/0059432 A1 | 3/2012 | Emborg et al. |
| 2012/0071250 A1 | 3/2012 | O'Neil et al. |
| 2012/0071950 A1 | 3/2012 | Archer |
| 2012/0083709 A1 | 4/2012 | Parker et al. |
| 2012/0101326 A1 | 4/2012 | Simon et al. |
| 2012/0109251 A1 | 5/2012 | Lebedev et al. |
| 2012/0109295 A1 | 5/2012 | Fan |
| 2012/0116476 A1 | 5/2012 | Kothandaraman |
| 2012/0123223 A1 | 5/2012 | Freeman et al. |
| 2012/0123293 A1 | 5/2012 | Shah et al. |
| 2012/0126392 A1 | 5/2012 | Kalvesten et al. |
| 2012/0136408 A1 | 5/2012 | Grill et al. |
| 2012/0165899 A1 | 6/2012 | Gliner |
| 2012/0172222 A1 | 7/2012 | Artigas Puerto |
| 2012/0172246 A1 | 7/2012 | Nguyen et al. |
| 2012/0172946 A1 | 7/2012 | Alataris et al. |
| 2012/0179222 A1 | 7/2012 | Jaax et al. |
| 2012/0185020 A1 | 7/2012 | Simon et al. |
| 2012/0197338 A1 | 8/2012 | Su et al. |
| 2012/0203055 A1 | 8/2012 | Pletnev |
| 2012/0203131 A1 | 8/2012 | DiLorenzo |
| 2012/0221073 A1 | 8/2012 | Southwell et al. |
| 2012/0232615 A1 | 9/2012 | Barolat et al. |
| 2012/0252380 A1 | 10/2012 | Kawakita |
| 2012/0252874 A1 | 10/2012 | Feinstein et al. |
| 2012/0259380 A1 | 10/2012 | Pyles |

(56) References Cited

U.S. PATENT DOCUMENTS

| | | |
|---|---|---|
| 2012/0271372 A1 | 10/2012 | Osorio |
| 2012/0277824 A1 | 11/2012 | Li |
| 2012/0277834 A1 | 11/2012 | Mercanzini et al. |
| 2012/0283697 A1 | 11/2012 | Kim et al. |
| 2012/0302821 A1 | 11/2012 | Burnett |
| 2012/0310305 A1 | 12/2012 | Kaula et al. |
| 2012/0310315 A1 | 12/2012 | Savage et al. |
| 2012/0330321 A1 | 12/2012 | Johnson et al. |
| 2012/0330391 A1 | 12/2012 | Bradley et al. |
| 2013/0012853 A1 | 1/2013 | Brown |
| 2013/0013041 A1 | 1/2013 | Glukhovsky et al. |
| 2013/0026640 A1 | 1/2013 | Ito et al. |
| 2013/0030312 A1 | 1/2013 | Keel et al. |
| 2013/0030319 A1 | 1/2013 | Hettrick et al. |
| 2013/0030501 A1 | 1/2013 | Feler et al. |
| 2013/0035745 A1 | 2/2013 | Ahmed et al. |
| 2013/0053734 A1 | 2/2013 | Barriskill et al. |
| 2013/0053922 A1 | 2/2013 | Ahmed et al. |
| 2013/0066392 A1 | 3/2013 | Simon et al. |
| 2013/0085317 A1 | 4/2013 | Feinstein |
| 2013/0085361 A1 | 4/2013 | Mercanzini et al. |
| 2013/0096640 A1 | 4/2013 | Possover |
| 2013/0096661 A1 | 4/2013 | Greenberg et al. |
| 2013/0096662 A1 | 4/2013 | Swanson |
| 2013/0110196 A1 | 5/2013 | Alataris et al. |
| 2013/0116751 A1 | 5/2013 | Moffitt et al. |
| 2013/0123568 A1 | 5/2013 | Hamilton et al. |
| 2013/0123659 A1 | 5/2013 | Bartol et al. |
| 2013/0138167 A1 | 5/2013 | Bradley et al. |
| 2013/0165991 A1 | 6/2013 | Kim et al. |
| 2013/0197408 A1 | 8/2013 | Goldfarb et al. |
| 2013/0204324 A1 | 8/2013 | Thacker et al. |
| 2013/0211477 A1 | 8/2013 | Cullen et al. |
| 2013/0237948 A1 | 9/2013 | Donders et al. |
| 2013/0253222 A1 | 9/2013 | Nakao |
| 2013/0253229 A1 | 9/2013 | Sawant et al. |
| 2013/0253299 A1 | 9/2013 | Weber et al. |
| 2013/0253611 A1 | 9/2013 | Lee et al. |
| 2013/0268016 A1 | 10/2013 | Xi et al. |
| 2013/0268021 A1 | 10/2013 | Moffitt |
| 2013/0281890 A1 | 10/2013 | Mishelevich |
| 2013/0289446 A1 | 10/2013 | Stone et al. |
| 2013/0289650 A1 | 10/2013 | Karlsson et al. |
| 2013/0289664 A1 | 10/2013 | Johanek |
| 2013/0289667 A1 | 10/2013 | Wacnik et al. |
| 2013/0296965 A1 | 11/2013 | Mokelke et al. |
| 2013/0303873 A1 | 11/2013 | Voros et al. |
| 2013/0304159 A1 | 11/2013 | Simon et al. |
| 2013/0310211 A1 | 11/2013 | Wilton et al. |
| 2013/0310911 A1 | 11/2013 | Tai et al. |
| 2014/0005753 A1 | 1/2014 | Carbunaru |
| 2014/0031893 A1 | 1/2014 | Walker et al. |
| 2014/0046407 A1 | 2/2014 | Ben-ezra et al. |
| 2014/0058292 A1 | 2/2014 | Alford et al. |
| 2014/0058490 A1 | 2/2014 | DiMarco |
| 2014/0066950 A1 | 3/2014 | MacDonald et al. |
| 2014/0067007 A1 | 3/2014 | Drees et al. |
| 2014/0067354 A1 | 3/2014 | Kaula et al. |
| 2014/0074190 A1 | 3/2014 | Griffith |
| 2014/0081011 A1 | 3/2014 | Vaught et al. |
| 2014/0081071 A1 | 3/2014 | Simon et al. |
| 2014/0088674 A1 | 3/2014 | Bradley |
| 2014/0100633 A1 | 4/2014 | Mann et al. |
| 2014/0107397 A1 | 4/2014 | Simon et al. |
| 2014/0107398 A1 | 4/2014 | Simon et al. |
| 2014/0114374 A1 | 4/2014 | Rooney et al. |
| 2014/0163640 A1 | 6/2014 | Edgerton et al. |
| 2014/0172045 A1 | 6/2014 | Yip et al. |
| 2014/0180361 A1 | 6/2014 | Burdick et al. |
| 2014/0213842 A1 | 7/2014 | Simon et al. |
| 2014/0228905 A1 | 8/2014 | Bolea |
| 2014/0236257 A1 | 8/2014 | Parker et al. |
| 2014/0243923 A1 | 8/2014 | Doan et al. |
| 2014/0277271 A1 | 9/2014 | Chan et al. |
| 2014/0296752 A1 | 10/2014 | Edgerton et al. |
| 2014/0303901 A1 | 10/2014 | Sadeh |
| 2014/0316484 A1 | 10/2014 | Edgerton et al. |
| 2014/0316503 A1 | 10/2014 | Tai et al. |
| 2014/0324118 A1 | 10/2014 | Simon et al. |
| 2014/0330067 A1 | 11/2014 | Jordan |
| 2014/0330335 A1 | 11/2014 | Errico et al. |
| 2014/0336722 A1 | 11/2014 | Rocon de Lima et al. |
| 2014/0357936 A1 | 12/2014 | Simon et al. |
| 2015/0005840 A1 | 1/2015 | Pal et al. |
| 2015/0065559 A1 | 3/2015 | Feinstein et al. |
| 2015/0066111 A1 | 3/2015 | Blum et al. |
| 2015/0165226 A1 | 6/2015 | Simon et al. |
| 2015/0182784 A1 | 7/2015 | Barriskill et al. |
| 2015/0190634 A1 | 7/2015 | Rezai et al. |
| 2015/0196231 A1 | 7/2015 | Ziaie et al. |
| 2015/0217120 A1 | 8/2015 | Nandra et al. |
| 2015/0231396 A1 | 8/2015 | Burdick et al. |
| 2015/0265830 A1 | 9/2015 | Simon et al. |
| 2015/0328462 A1 | 11/2015 | Griffith |
| 2016/0001096 A1 | 1/2016 | Mishelevich |
| 2016/0030737 A1 | 2/2016 | Gerasimenko et al. |
| 2016/0030748 A1 | 2/2016 | Edgerton et al. |
| 2016/0030750 A1 | 2/2016 | Bokil et al. |
| 2016/0045727 A1 | 2/2016 | Rezai et al. |
| 2016/0045731 A1 | 2/2016 | Simon et al. |
| 2016/0074663 A1 | 3/2016 | De Ridder |
| 2016/0121109 A1 | 5/2016 | Edgerton et al. |
| 2016/0121114 A1 | 5/2016 | Simon et al. |
| 2016/0121116 A1 | 5/2016 | Simon et al. |
| 2016/0121121 A1 | 5/2016 | Mashiach |
| 2016/0143588 A1 | 5/2016 | Hoitink et al. |
| 2016/0157389 A1 | 6/2016 | Hwang |
| 2016/0157769 A1 | 6/2016 | Min et al. |
| 2016/0175586 A1 | 6/2016 | Edgerton et al. |
| 2016/0220813 A1 | 8/2016 | Edgerton et al. |
| 2016/0235977 A1 | 8/2016 | Lu et al. |
| 2016/0271413 A1 | 9/2016 | Vallejo et al. |
| 2016/0279418 A1 | 9/2016 | Courtine et al. |
| 2016/0279429 A1 | 9/2016 | Hershey et al. |
| 2016/0310739 A1 | 10/2016 | Burdick et al. |
| 2017/0007320 A1 | 1/2017 | Levin et al. |
| 2017/0007831 A1 | 1/2017 | Edgerton et al. |
| 2017/0128729 A1 | 5/2017 | Netoff et al. |
| 2017/0157389 A1 | 6/2017 | Tai et al. |
| 2017/0157396 A1 | 6/2017 | Dixon et al. |
| 2017/0161454 A1 | 6/2017 | Grill et al. |
| 2017/0165497 A1 | 6/2017 | Lu |
| 2017/0173326 A1 | 6/2017 | Bloch et al. |
| 2017/0189686 A1 | 7/2017 | Steinke et al. |
| 2017/0246450 A1 | 8/2017 | Liu et al. |
| 2017/0246452 A1 | 8/2017 | Liu et al. |
| 2017/0266455 A1 | 9/2017 | Steinke |
| 2017/0274209 A1 | 9/2017 | Edgerton et al. |
| 2017/0296837 A1 | 10/2017 | Jin |
| 2017/0361093 A1 | 12/2017 | Yoo et al. |
| 2018/0056078 A1 | 3/2018 | Kashyap et al. |
| 2018/0085583 A1 | 3/2018 | Zhang et al. |
| 2018/0104479 A1* | 4/2018 | Grill .................. G16H 20/30 |
| 2018/0110992 A1 | 4/2018 | Parramon et al. |
| 2018/0125416 A1 | 5/2018 | Schwarz et al. |
| 2018/0178008 A1 | 6/2018 | Bouton et al. |
| 2018/0185642 A1 | 7/2018 | Lu |
| 2018/0185648 A1 | 7/2018 | Nandra et al. |
| 2018/0193655 A1 | 7/2018 | Zhang et al. |
| 2018/0229037 A1 | 8/2018 | Edgerton et al. |
| 2018/0229038 A1 | 8/2018 | Burdick et al. |
| 2018/0236240 A1 | 8/2018 | Harkema et al. |
| 2018/0256906 A1 | 9/2018 | Pivonka et al. |
| 2018/0280693 A1 | 10/2018 | Edgerton et al. |
| 2018/0353755 A1 | 12/2018 | Edgerton et al. |
| 2018/0361146 A1 | 12/2018 | Gerasimenko et al. |
| 2019/0009094 A1 | 1/2019 | Zhang et al. |
| 2019/0022371 A1 | 1/2019 | Chang et al. |
| 2019/0033622 A1 | 1/2019 | Olgun et al. |
| 2019/0160294 A1 | 5/2019 | Peterson et al. |
| 2019/0167987 A1 | 6/2019 | Lu et al. |
| 2019/0192864 A1 | 6/2019 | Koop et al. |
| 2019/0247650 A1 | 8/2019 | Tran |
| 2019/0381313 A1 | 12/2019 | Lu |

(56) References Cited

U.S. PATENT DOCUMENTS

| | | |
|---|---|---|
| 2019/0381328 A1 | 12/2019 | Wechter et al. |
| 2020/0155865 A1 | 5/2020 | Lu |
| 2020/0228901 A1 | 7/2020 | Baek |
| 2021/0069052 A1 | 3/2021 | Burke |
| 2021/0153942 A1 | 5/2021 | Scheltienne et al. |
| 2021/0187278 A1 | 6/2021 | Lu |
| 2021/0236837 A1 | 8/2021 | Lu |
| 2021/0378991 A1 | 12/2021 | Lu |

FOREIGN PATENT DOCUMENTS

| | | |
|---|---|---|
| CA | 2864473 A1 | 5/2013 |
| CA | 2823592 A1 | 11/2021 |
| CN | 101227940 A | 7/2008 |
| CN | 103263727 A | 8/2013 |
| CN | 104307098 A | 1/2015 |
| EP | 0630987 A1 | 12/1994 |
| EP | 2130326 A1 | 12/2009 |
| EP | 2141851 A2 | 1/2010 |
| EP | 2160127 A1 | 3/2010 |
| EP | 2178319 A1 | 4/2010 |
| EP | 2192897 A1 | 6/2010 |
| EP | 2226114 A1 | 9/2010 |
| EP | 2258496 A1 | 12/2010 |
| EP | 2361631 A1 | 8/2011 |
| EP | 2368401 A1 | 9/2011 |
| EP | 2387467 A1 | 11/2011 |
| EP | 2396995 A1 | 12/2011 |
| EP | 2397788 A1 | 12/2011 |
| EP | 2445990 A2 | 5/2012 |
| EP | 2471518 A2 | 7/2012 |
| EP | 2475283 A1 | 7/2012 |
| EP | 2486897 A2 | 8/2012 |
| EP | 2626051 A1 | 8/2013 |
| EP | 2628502 A1 | 8/2013 |
| EP | 2661307 A2 | 11/2013 |
| EP | 2688642 A2 | 1/2014 |
| EP | 2810689 A1 | 12/2014 |
| EP | 2810690 A1 | 12/2014 |
| EP | 2868343 A1 | 5/2015 |
| EP | 2966422 A1 | 1/2016 |
| EP | 2968940 A1 | 1/2016 |
| EP | 3184145 A1 | 6/2017 |
| EP | 3323468 A1 | 5/2018 |
| EP | 3328481 A1 | 6/2018 |
| EP | 3527258 A1 | 8/2019 |
| JP | H0326620 A | 2/1991 |
| JP | 3184145 B2 | 7/2001 |
| JP | 2002200178 A | 7/2002 |
| JP | 2004065529 A | 3/2004 |
| JP | 2007526798 A | 9/2007 |
| JP | 2008067917 A | 3/2008 |
| JP | 2008543429 A | 12/2008 |
| JP | 2014514043 A | 6/2014 |
| JP | 6132856 B2 | 3/2015 |
| JP | 2016506255 A | 3/2016 |
| JP | 2017104685 A | 6/2017 |
| JP | 2017525509 A | 9/2017 |
| JP | 2018524113 A | 8/2018 |
| RU | 2130326 C1 | 5/1999 |
| RU | 2141851 C1 | 11/1999 |
| RU | 2160127 C1 | 12/2000 |
| RU | 2178319 C2 | 1/2002 |
| RU | 2192897 C2 | 11/2002 |
| RU | 2001102533 | 11/2002 |
| RU | 2226114 C1 | 3/2004 |
| RU | 2258496 C2 | 8/2005 |
| RU | 2361631 C2 | 7/2009 |
| RU | 2368401 C1 | 9/2009 |
| RU | 2387467 C1 | 4/2010 |
| RU | 2396995 C2 | 8/2010 |
| RU | 2397788 C2 | 8/2010 |
| RU | 2445990 C1 | 3/2012 |
| RU | 2471518 C2 | 1/2013 |
| RU | 2475283 C2 | 2/2013 |
| RU | 2661307 C1 | 7/2018 |
| WO | WO 1997047357 A1 | 12/1997 |
| WO | WO 2002034331 A2 | 5/2002 |
| WO | WO 2002092165 A1 | 11/2002 |
| WO | WO 2003005887 A2 | 1/2003 |
| WO | WO 2003026735 A2 | 4/2003 |
| WO | WO 2003092795 A1 | 11/2003 |
| WO | WO 2004087116 A2 | 10/2004 |
| WO | WO 2005002663 A2 | 1/2005 |
| WO | WO 2005051306 A2 | 6/2005 |
| WO | WO 2005065768 A1 | 7/2005 |
| WO | WO 2005087307 A2 | 9/2005 |
| WO | WO 2006138069 A1 | 12/2006 |
| WO | WO 2007007058 A1 | 1/2007 |
| WO | WO 2007012114 A1 | 2/2007 |
| WO | WO 2007047852 A2 | 4/2007 |
| WO | WO 2007081764 A2 | 7/2007 |
| WO | WO 2007107831 A2 | 9/2007 |
| WO | WO 2008070807 A3 | 6/2008 |
| WO | WO 2008075294 A1 | 6/2008 |
| WO | WO 2008109862 A2 | 9/2008 |
| WO | WO 2008121891 A1 | 10/2008 |
| WO | WO 2009042217 A1 | 4/2009 |
| WO | WO 2009111142 A2 | 9/2009 |
| WO | WO 20100021977 A1 | 2/2010 |
| WO | WO 2010055421 A1 | 5/2010 |
| WO | WO 2010114998 A1 | 10/2010 |
| WO | WO 2010124128 A1 | 10/2010 |
| WO | WO 2011005607 A1 | 1/2011 |
| WO | WO 2011136875 A1 | 11/2011 |
| WO | WO 2012075195 A1 | 6/2012 |
| WO | WO 2012080964 A1 | 6/2012 |
| WO | WO 2012094346 A2 | 7/2012 |
| WO | WO 2012100260 A2 | 7/2012 |
| WO | WO 2012129574 A2 | 9/2012 |
| WO | WO 2013071307 A1 | 5/2013 |
| WO | WO 2013071309 A1 | 5/2013 |
| WO | WO 2013152124 A1 | 10/2013 |
| WO | WO 2013179230 A1 | 12/2013 |
| WO | WO 2013188965 A1 | 12/2013 |
| WO | WO 2014005075 A1 | 1/2014 |
| WO | WO 2014031142 A1 | 2/2014 |
| WO | WO 2014089299 A2 | 6/2014 |
| WO | WO 2014144785 A1 | 9/2014 |
| WO | WO 2014149895 A1 | 9/2014 |
| WO | WO 2014205356 A2 | 12/2014 |
| WO | WO 2014209877 A1 | 12/2014 |
| WO | WO 2015000800 A1 | 1/2015 |
| WO | WO 2015048563 A2 | 4/2015 |
| WO | WO 2015063127 A1 | 5/2015 |
| WO | WO 2015106286 A1 | 7/2015 |
| WO | WO 2016029159 A2 | 2/2016 |
| WO | WO 2016033369 A1 | 3/2016 |
| WO | WO 2016033372 A1 | 3/2016 |
| WO | WO 2016064761 A1 | 4/2016 |
| WO | WO 2016110804 A1 | 7/2016 |
| WO | WO 2016112398 A1 | 7/2016 |
| WO | WO 2016172239 A1 | 10/2016 |
| WO | WO 2017011410 A1 | 1/2017 |
| WO | WO 2017024276 A1 | 2/2017 |
| WO | WO 2017035512 A1 | 3/2017 |
| WO | WO 2017044904 A1 | 3/2017 |
| WO | WO 2017058913 A1 | 4/2017 |
| WO | WO 2017062508 A1 | 4/2017 |
| WO | WO 2017117450 A1 | 7/2017 |
| WO | WO 2017146659 A1 | 8/2017 |
| WO | WO 2018039296 A2 | 3/2018 |
| WO | WO 2018106843 A1 | 6/2018 |
| WO | WO 2018140531 A1 | 8/2018 |
| WO | WO 2018217791 A1 | 11/2018 |
| WO | WO 2012050200 A1 | 4/2019 |
| WO | WO 2019211314 A1 | 11/2019 |
| WO | WO 2020041502 A1 | 2/2020 |

(56) References Cited

FOREIGN PATENT DOCUMENTS

| | | |
|---|---|---|
| WO | WO 2020041633 A1 | 2/2020 |
| WO | WO 2020236946 A1 | 11/2020 |

OTHER PUBLICATIONS

Bizzi, E. et al., "Modular Organization of Motor Behavior," Trends in Neurosciences, vol. 18, No. 10, Oct. 1995, 8 pages.
Rattay, F. et al., "Epidural electrical stimulation of posterior structures of the human lumbosacral cord: 2. quantitative analysis by computer modeling," Spinal Cord, vol. 38, No. 8, Aug. 2000, 17 pages.
Courtine, G. et al., "Transformation of nonfunctional spinal circuits into functional states after the loss of brain input," Nature Neuroscience, vol. 12, No. 10, Oct. 2009, Published Online Sep. 20, 2009, 12 pages.
Harkema, S. et al., "Effect of Epidural stimulation of the lumbosacral spinal cord on voluntary movement, standing, and assisted stepping after motor complete paraplegia: a case study," Lancet, vol. 377, No. 9781, Jun. 4, 2011, Available Online May 19, 2011, 17 pages.
Van Den Brand, R. et al., "Restoring Voluntary Control of Locomotion after Paralyzing Spinal Cord Injury," Science Magazine, vol. 336, No. 6085, Jun. 1, 2012, 5 pages.
Capogrosso, M. et al., "A Computational Model for Epidural Electrical Stimulation of Spinal Sensorimotor Circuits," Journal of Neuroscience, vol. 33, No. 49, Dec. 4, 2013, 15 pages.
Levine, A. et al., "Identification of cellular node for motor control pathways," Nature Neuroscience, vol. 17, No. 4, Apr. 2014, Available Online Mar. 9, 2014, 22 pages.
Angeli, C. et al., "Altering spinal cord excitability enables voluntary movements after chronic complete paralysis in humans," Brain: A Journal of Neurology, vol. 137, No. 5, May 1, 2014, Published Online Apr. 8, 2014, 16 pages.
Danner, S. et al., "Human spinal locomotor control is based on flexibly organized burst generators," Brain: A Journal of Neurology, vol. 138, No. 3, Mar. 1, 2015, Published Online Jan. 12, 2015, 12 pages.
Capogrosso, M. et al., "A Brain-Spinal Interface Alleviating Gait Deficits after Spinal Cord Injury in Primates," Nature, vol. 539, No. 7628, Nov. 10, 2016, 39 pages.
Abernethy, J. et al., "Competing in the Dark: An Efficient Algorithm for Bandit Linear Optimization", Conference on Learning Theory, (2008), 13 pages.
Ada, L. et al., "Mechanically assisted walking with body weight support results in more independent walking than assisted overground walking in non-ambulatory patients early after stroke: a systematic review," Journal of Physiotherapy, vol. 56, No. 3, (Sep. 2010), 9 pages.
Alto, L. et al., "Chemotropic Guidance Facilitates Axonal Regeneration and Synapse Formation after Spinal Cord Injury," Nature Neuroscience, vol. 12, No. 9, Published Online Aug. 2, 2009, (Sep. 2009), 22 pages.
Anderson, K., "Targeting Recovery: Priorities of the Spinal Cord-Injured Population," Journal of Neurotrauma, vol. 21, No. 10, (Oct. 2004), 13 pages.
Auer, P. et al., "Finite-time Analysis of the Multiarmed Bandit Problem", Machine Learning, vol. 47, No. 2, (2002), pp. 235-256.
Auer, P. "Using Confidence Bounds for Exploitation-Exploration Trade-offs", Journal of Machine Learning Research, vol. 3, (2002), pp. 397-422.
Avery, M. Large-Scale Neural Network Models of Neuromodulation and Attention (Order No. 3565843). Available from ProQuest Dissertations and Theses Professional. (1417763263). Retrieved from https://diaog.proquest.com/professional/docview/1417763236?accountid=1314444 (Year: 2013), 158 pages.
Azimi, J. et al., "Batch Bayesian Optimization via Simulation Matching", In Advances in Neural Information Processing Systems (NIPS), (2010), 9 pages.
Azimi, J. et al., "Hybrid Batch Bayesian Optimization", In Proceedings of the 29th International Conference on Machine Learning, (2012), 12 pages.
Azimi, J. et al., "Batch Active Learning via Coordinated Matching", In Proceedings of the 29th International Conference on Machine Learning, (2012), 8 pages.
Barbeau, H. et al., "Recovery of locomotion after chronic spinalization in the adult cat", Brain Research, vol. 412, No. 1, (May 26, 1987), 12 pages.
Bareyre, F. et al., "The injured spinal cord spontaneously forms a new intraspinal circuit in adult rats," Nature Neuroscience, vol. 7, No. 3, Published Online Feb. 15, 2004, (Mar. 2004), 9 pages.
Basso, D. et al., "MASCIS Evaluation of Open Field Locomotor Scores: Effects of Experience and Teamwork on Reliability," Journal of Neurotrauma, vol. 13, No. 7, (Jul. 1996), 17 pages.
Brochu, et al., "A Tutorial on Bayesian Optimization of Expensive Cost Functions, with Application to Active User Modeling and Hierarchical Reinforcement Learning", In TR-2009-23, UBC, (2009), 49 pages.
Brosamle, C. et al., "Cells of Origin, Course, and Termination Patterns of the Ventral, Uncrossed Component of the Mature Rat Corticospinal Tract," The Journal of Comparative Neurology, vol. 386, No. 2, (Sep. 22, 1997), 11 pages.
Bubeck, S. et al., "Online Optimization in X-Armed Bandits", Advances in Neural Information Processing Systems (NIPS), (2008), 8 pages.
Bubeck, S. et al., "Pure Exploration in Finitely-Armed and Continuous-Armed Bandits problems" In ALT, (2009), 35 pages.
Burke, R., "Group la Synaptic Input to Fast and Slow Twitch Motor Units of Cat Triceps Surae", The Journal of Physiology, vol. 196, vol. 3, (Jun. 1, 1968), 26 pages.
Cai, L. et al., "Implications of Assist-As-Needed Robotic Step Training after a Complete Spinal Cord Injury on Intrinsic Strategies of Motor Learning", The Journal of Neuroscience, vol. 26, No. 41, (Oct. 11, 2006), 5 pages.
Carhart, M. et al., "Epidural Spinal-Cord Stimulation Facilitates Recovery of Functional Walking Following Incomplete Spinal-Cord Injury," IEEE Transactions on Neural Systems and Rehabilitation Engineering, vol. 12, No. 1, (Mar. 15, 2004), 11 pages.
Colgate, E. et al., "An Analysis of Contact Instability in Terms of Passive Physical Equivalents," Proceedings of the 1989 IEEE International Conference on Robotics and Automation, Scottsdale, Arizona, (May 14, 1989), 6 pages.
Courtine, G. et al., "Can experiments in nonhuman primates expedite the translation of treatments for spinal cord injury in humans?", Nature Medicine, vol. 13, No. 5, (May 2007), 13 pages.
Courtine, G. et al., "Recovery of supraspinal control of stepping via indirect propriospinal relay connections after spinal cord injury," Nature Medicine, vol. 14, No. 1, (Jan. 6, 2008), 6 pages.
Cowley, K. et al., "Propriospinal neurons are sufficient for bulbospinal transmission of the locomotor command signal in the neonatal rat spinal cord," The Journal of Physiology, vol. 586, No. 6, Published Online Jan. 31, 2008, (Mar. 15, 2008), 13 pages.
Dani, V. et al., "Stochastic Linear Optimization Under Bandit Feedback", In Proceedings of the 21st Annual Conference on Learning Theory (COLT), (2008), 15 pages.
Danner, S. M. et al., "Body Position Influences Which neural structures are recruited by lumbar transcutaneous spinal cord stimulation", PLoS ONE, vol. 11, No. 1, (2016), 13 pages.
Dimitrijevic, M. M. et al., "Evidence for a Spinal Central Pattern Generator in Humans", Annals New York Academy Sciences, vol. 860, (1998), pp. 360-376.
Dimitrijevic, M. M. et al., "Clinical Elements for the Neuromuscular Stimulation and Functional Electrical Stimulation protocols in the Practice of Neurorehabilitation", Artificial Organs, vol. 26, No. 3, (2002), pp. 256-259.
Dimitrijevic, M. R. et al., "Electrophysiological characteristics of H-reflexes elicited by percutaneous stimulation of the cauda equina", Abstract No. 4927, 34th Annual Meeting of the Society for Neuroscience, San Diego, CA (2004), 1 page.

(56) References Cited

OTHER PUBLICATIONS

Drew, T. et al., "Cortical mechanisms involved in visuomotor coordination during precision walking," Brain Research Reviews, vol. 57, No. 1, Published Online Aug. 22, 2007, (Jan. 2007), 13 pages.
Duschau-Wicke, A. et al., "Patient-cooperative control increases active participation of individuals with SCI during robot-aided gait training," Journal of NeuroEngineering and Rehabilitation, vol. 7, No. 43, (Sep. 10, 2010), 13 pages.
Edgerton, V. et al., "Robotic Training and Spinal Cord Plasticity," Brain Research Bulletin, vol. 78, No. 1, Published Online Nov. 14, 2008, (Jan. 15, 2009), 19 pages.
Edgerton, V. et al., "Training Locomotor Networks," Brain Research Reviews, vol. 57, Published Online Sep. 16, 2007, (Jan. 2008), 25 pages.
European Communication and Extended European Search Report dated May 28, 2020 in counterpart European Patent Application No. 19211698.6, 6 pages.
Fleshman, J. et al., "Electronic Architecture of Type-Identified a-Motoneurons in the Cat Spinal Cord," Journal of Neurophysiology, vol. 60, No. 1, (Jul. 1, 1988), 26 pages.
Frey, M. et al., "A Novel Mechatronic Body Weight Support System," IEEE Transactions on Neural Systems and Rehabilitation Engineering, vol. 14, No. 3, (Sep. 18, 2006), 11 pages.
Fuentes, R. et al., "Spinal Cord Stimulation Restores Locomotion in Animal Models of Parkinson's Disease," Science, vol. 323, No. 5921, (Mar. 20, 2009), 14 pages.
Ganley, K. J. et al., "Epidural Spinal Cord Stimulation Improves Locomotor Performance in Low ASIA C, Wheelchair-Dependent, Spinal Cord-Injured Individuals: Insights from Metabolic Response", Top. Spinal Cord Inj. Rehabil., vol. 11, No. 2, (2005), pp. 60-63.
Gerasimenko, Yu. P. et al., "Control of Locomotor Activity in Humans and Animals in the Absence of Supraspinal Influences", Neuroscience and Behavioral Physiology, vol. 32, No. 4, (2002), pp. 417-423.
Gerasimenko, Yu. P. et al., "Noninvasive Reactivation of Motor Descending Control after Paralysis", Journal of Neurotrauma, vol. 32, (2015), 13 pages.
Gilja, V. et al., "A high-performance neural prosthesis enabled by control algorithm design," Nature Neuroscience, vol. 15, No. 12, Published Online Nov. 18, 2012, (Dec. 2012), 56 pages.
Gittins, J. C., "Bandit Processes and Dynamic Allocation Indices", Journal of the Royal Statistical Society B, vol. 41, No. 2, (1979), pp. 148-177.
Guyatt, G. H. et al., "The 6-minute walk: a new measure of exercise capacity in patients with chronic heart failure," Canadian Medical Association Journal, vol. 132, No. 8, (Apr. 15, 1985), 5 pages.
Hagglund, M. et al., "Activation of groups of excitatory neurons in the mammalian spinal cord or hindbrain evokes locomotion," Nature Neuroscience, vol. 13, No. 2, Published Online Jan. 17, 2010, (Feb. 2010), 8 pages.
Harrison, P. et al., "Individual Excitatory Post-Synaptic Potentials Due to Muscle Spindle la Afferents in Cat Triceps Surae Motoneurones," The Journal of Physiology, vol. 312, No. 1, (Mar. 1981), pp. 455-470.
Harkema, S. et al., "Human Lumbosacral Spinal Cord Interprets Loading During Stepping," Journal of Neurophysiology, vol. 77, No. 2, (Feb. 1, 1997), 15 pages.
Hashtrudi-Zaad, K. et al., "On the Use of Local Force Feedback for Transparent Teleoperation," Proceedings of the 1999 IEEE International Conference on Robotics and Automation, (May 10, 1999), 7 pages.
Herman, R. et al., "Spinal cord stimulation facilitates functional walking in a chronic, incomplete spinal cord injured," Spinal Cord, vol. 40, No. 2, (2002), 4 pages.
Hennig, P. et al., "Entropy search for information-efficient global optimization" Journal of Machine Learning Research (JMLR), vol. 13, (Jun. 2012), pp. 1809-1837.
Hidler, J. et al., "ZeroG: Overground gait and balance training system," Journal of Rehabilitation Research & Development, vol. 48, No. 4, Available as Early as Jan. 1, 2011, (2011), 12 pages.
Hines, M. L. et al., "The Neuron Simulation Environment," Neural Computation, vol. 9, No. 6, (Aug. 15, 1997), 26 pages.
Hofstoetter, U. S. et al., "Modification of Reflex Responses to Lumbar Posterior Root Stimulation by Motor Tasks in Healthy Subjects", Artificial Organs, vol. 32, No. 8, (2008), pp. 644-648.
Hofstoetter, U. S. et al., "Model of spinal cord reflex circuits in humans: Stimulation frequency-dependence of segmental activities and their interactions", Second Congress International Society of Intraoperative Neurophysiology (ISIN), Dubrovnik, Croatia, (2009), 149 pages.
Hofstoetter, U. S. et al., "Effects of transcutaneous spinal cord stimulation on voluntary locomotor activity in an incomplete spinal cord injured individual", Biomed Tech, vol. 58 (Suppl. 1), (2013), 3 pages.
Hofstoetter, U. S. et al., "Modification of spasticity by transcutaneous spinal cord stimulation in individuals with incomplete spinal cord injury", The Journal of Spinal Cord Medicine, vol. 37, No. 2, (2014), pp. 202-211.
Ivanenko, Y. P. et al., "Temporal Components of the Motor Patterns Expressed by the Human Spinal Cord Reflect Foot Kinematics," Journal of Neurophysiology, vol. 90, No. 5, Nov. 2003, Published Online Jul. 9, 2003, (2003), 11 pages.
Jarosiewicz, B. et al., "Supplementary Materials for Virtual typing by people with tetraplegia using a self-calibrating intracortical brain-computer interface," Science Translational Medicine, vol. 7, No. 313, (Nov. 11, 2015), 26 pages.
Jarosiewicz, B. et al., "Virtual typing by people with tetraplegia using a self-calibrating intracortical brain-computer interface," Science Translational Medicine, vol. 7, No. 313, (Nov. 11, 2015), 11 pages.
Jilge, B. et al., "Initiating extension of the lower limbs in subjects with complete spinal cord injury by epidural lumbar cord stimulation", Exp Brain Res., vol. 154, (2004), pp. 308-326.
Johnson, W. L. et al., "Application of a Rat Hindlimb Model: A Prediction of Force Spaces Reachable Through Stimulation of Nerve Fascicles," IEEE Transactions on Bio-Medical Engineering, vol. 58, No. 12, Available Online Jan. 17, 2011, (Dec. 2011), 22 pages.
Jones, K. E. et al., "Computer Simulation of the Responses of Human Motoneurons to Composite 1A EPSPS: Effects of Background Firing Rate," The Journal of Physiology, vol. 77, No. 1, (1997), 16 pages.
Jones, D. R. et al., "Efficient Global Optimization of Expensive Black-Box Functions", Journal of Global Optimization, vol. 13, (1998), pp. 455-492.
Kakulas, B., "A Review of the Neuropathology of Human Spinal Cord Injury with Emphasis on Special Features," Proceedings of the Donald Munro Memorial Lecture at the American Paraplegia Society 44th Annual Conference, Sep. 9, 1998, Las Vegas, Nevada, (1998), 6 pages.
Kirkwood, P., "Neuronal Control of Locomotion: "From Mollusc to Man", G.N. Orlovsky, T.G. Deliagina and S. Grillner. Oxford University Press, Oxford, 1999. ISBN 0198524056 (Hbk), 322 pp.," Clinical Neurophysiology, vol. 111, No. 8, Published Online Jul. 17, 2000, (Aug. 1, 2000), 2 pages.
Kleinberg, R. et al., "Multi-armed bandits in metric spaces", in STOC, Computer and Automation Research Institute of the Hungarian Academy of Sciences, Budapest, Hungary, (2008), pp. 681-690.
Kocsis, L. et al. "Bandit Based Monte-Carlo Planning", European Conference on Machine Learning, Springer, Berlin, Heidelberg, (Sep. 2006), pp. 282-293.
Krassioukov, A. et al., "A Systematic Review of the Management of Autonomic Dysreflexia Following Spinal Cord Injury," Archives of Physical Medicine and Rehabilitation, vol. 90, No. 4, (Apr. 2009), 27 pages.
Krassioukov, A. et al., "A Systematic Review of the Management of Orthostatic Hypotension Following Spinal Cord Injury," Archives of Physical Medicine and Rehabilitation, vol. 90, No. 5, (May 2009), 22 pages.

(56) References Cited

OTHER PUBLICATIONS

Krause, A. et al., "Near-optimal Nonmyopic Value of Information in Graphical Models", in UAI, (2005), 8 pages.

Krause, A. et al. "Near-Optimal Sensor Placements in Gaussian Processes: Theory, Efficient Algorithms and Empirical Studies", Journal of Machine Learning Research (JMLR), vol. 9, (Feb. 2008), pp. 235-284.

Krause, A. et al. "Contextual Gaussian Process Bandit Optimization", In Advances in Neural Information Processing Systems (NIPS), (2011), 9 pages.

Kwakkel, G. et al., "Effects of Robot-assisted therapy on upper limb recovery after stroke: A Systematic Review," Neurorehabilitation and Neural Repair, vol. 22, No. 2, Published Online Sep. 17, 2007, (Mar. 2008), 17 pages.

Ladenbauer, J. et al., "Stimulation of the human lumbar spinal cord with implanted and surface electrodes: a computer simulation study", IEEE Transactions on Neural Systems and Rehabilitation Engineering, vol. 18, No. 6, (2010), pp. 637-645.

Lavrov, I. et al., "Epidural Stimulation Induced Modulation of Spinal Locomotor Networks in Adult Spinal Rats," Journal of Neuroscience, vol. 28, No. 23, (Jun. 4, 2008), 8 pages.

Liu, J. et al., "Stimulation of the Parapyramidal Region of the Neonatal Rat Brain Stem Produces Locomotor-Like Activity Involving Spinal 5-$HT_7$ and 5-$HT_{2A}$ Receptors", Journal of Neurophysiology, vol. 94, No. 2, Published Online May 4, 2005, (Aug. 1, 2005), 13 pages.

Lizotte, D. et al., "Automatic gait optimization with Gaussian process regression", In IJCAI, (2007), pp. 944-949.

Lovely, R. et al., "Effects of Training on the Recovery of Full-Weight-Bearing Stepping in the Adult Spinal Cat," Experimental Neurology, vol. 92, No. 2, (May 1986), 15 pages.

Lozano, A. et al., "Probing and Regulating Dysfunctional Circuits Using Deep Brain Stimulation," Neuron, vol. 77, No. 3, (Feb. 6, 2013), 19 pages.

McIntyre, C. C. et al., "Modeling the Excitability of Mammalian Nerve Fibers: Influence of Afterpotentials on the Recovery Cycle," Journal of Neurophysiology, vol. 87, No. 2, (Feb. 2002), 12 pages.

Minassian, K. et al., "Stepping-like movements in humans with complete spinal cord injury induced by epidural stimulation of the lumbar cord: electromyographic study of compound muscle action potentials", Spinal Cord, vol. 42, (2004), pp. 401-416.

Minassian, K. et al., "Peripheral and central afferent input to the lumbar cord", Biocybemetics and Biomedical Engineering, vol. 25, No. 3, (2005), pp. 11-29.

Minassian, K. et al., "Human lumbar cord circuitries can be activated by extrinsic tonic input to generate locomotor-like activity", Human Movement Science, vol. 26, No. 2, (2007), pp. 275-295.

Minassian, K. et al., "Posterior root-muscle reflex", Second Congress International Society of Intraoperative Neurophysiology (ISIN), Dubrovnik, Croatia, (2009), pp. 77-80.

Minassian, K. et al., "Transcutaneous stimulation of the human lumbar spinal cord: Facilitating locomotor output in spinal cord injury", Society for Neuroscience, Conference Proceedings, Neuroscience 2010, San Diego, CA, Abstract Viewer/ Itinerary Planner No. 286. 19, Abstract & Poster attached (2010), 1 page.

Minassian, K. et al., "Neuromodulation of lower limb motor control in restorative neurology", Clinical Neurology and Neurosurgery, vol. 114, (2012), pp. 489-497.

Minassian et al., "Mechanisms of rhythm generation of the human lumbar spinal cord in repose to tonic stimulation without and with step-related sensory feedback", Biomed Tech, vol. 58, (Suppl. 1), (2013), 3 pages.

Minev, I. R. et al., "Electronic dura mater for long-term multimodal neural interfaces," Science Magazine, vol. 347, No. 6218, (Jan. 9, 2015), 64 pages.

Minoux, M., Accelerated greedy algorithms for maximizing submodular set functions. Optimization Techniques, LNCS, (1978), pp. 234-243.

Moraud, E., "Mechanisms Underlying the Neuromodulation of Spinal Circuits for Correcting Gait and Balance Deficits after Spinal Cord Injury," Neuron, vol. 89, No. 4, (2016), 15 pages.

Murg, M et al., "Epidural electric stimulation of posterior structures of the human lumbar spinal cord: 1. Muscle twitches—a functional method to define the site of stimulation", Spinal Cord, vol. 38, (2000), pp. 394-402.

Musienko, P. et al. "Multi-system neurorehabilitative strategies to restore motor functions following severe spinal cord injury," Experimental Neurology, vol. 235, No. 1, Published Online Sep. 7, 2011, (May 2012), 10 pages.

Musienko, P. et al., "Combinatory Electrical and Pharmacological Neuroprosthetic Interfaces to Regain Motor Function After Spinal Cord Injury," IEEE Transactions on Biomedical Engineering, vol. 56, No. 11, Published Online Jul. 24, 2009, (Nov. 2009), 5 pages.

Musienko, P. et al., "Controlling specific locomotor behaviors through multidimensional monoaminergic modulation of spinal circuitries," The Journal of Neuroscience, vol. 31, No. 25, (Jun. 22, 2011), 32 pages.

Musselman, K. et al., "Spinal Cord Injury Functional Ambulation Profile: A New Measure of Walking Ability," Neurorehabilitation and Neural Repair, vol. 25, No. 3, Published Online Feb. 25, 2011, (Mar. 2011), 9 pages.

Nandra, M. S. et al., "A parylene-based microelectrode array implant for spinal cord stimulation in rats", Conference Proceedings IEEE Eng. Med. Biol. Soc., (2011), pp. 1007-1010.

Nandra, M. S. et al., "A wireless microelectrode implant for spinal cord stimulation and recording in rats", Presentation Abstract, 2013.

Nessler, J. et al., "A Robotic Device for Studying Rodent Locomotion After Spinal Cord Injury," IEEE Transactions on Neural Systems and Rehabilitation Engineering, vol. 13, No. 4, (Dec. 12, 2005), 10 pages.

Pearson, K. G., "Generating the walking gait: role of sensory feedback," Progress in Brain Research, vol. 143, Chapter 12, Published Online Nov. 28, 2003, (2004), 7 pages.

Phillips, A. et al., "Perturbed and spontaneous regional cerebral blood flow responses to changes in blood pressure secondary high-level spinal cord injury: the effect of midodrine," Journal of Applied Physiology, vol. 116, No. 6, Available Online Jan. 16, 2014, (Mar. 15, 2014), 20 pages.

Phillips, A. et al., "Regional neurovascular coupling and cognitive performance in those with low blood pressure secondary to high-level spinal cord injury: improved by alpha-1 agonist midodrine hydrochloride," Journal of Cerebral Blood Flow & Metabolism, vol. 34, No. 5, (May 2014), 8 pages.

Phillips, A. A. et al., "Contemporary Cardiovascular Concerns after Spinal Cord Injury: Mechanisms, Maladaptations, and Management," Journal of Neurotrama, vol. 32, No. 24, (Dec. 15, 2015), 17 pages.

Pratt, G. et al., "Stiffness Isn't Everything," Proceedings of the Fourth International Symposium on Experimental Robotics, (Jun. 30, 1995), 6 pages.

Pratt, J. et al., "Series elastic actuators for high fidelity force control," Industrial Robot: An International Journal, vol. 29, No. 3, Available as Early as Jan. 1, 2002, (1995), 13 pages.

Prochazka, A. et al., "Ensemble firing of muscle afferents recorded during normal locomotion in cats," The Journal of Physiology, vol. 507, No. 1, (Feb. 15, 1998), 12 pages.

Prochazka, A. et al., "Models of ensemble filing of muscle spindle afferents recorded during normal locomotion in cats," The Journal of Physiology, vol. 507, No. 1, (Feb. 15, 1998), 15 pages.

Pudo, D. et al., "Estimating Intensity Fluctuations in High Repetition Rate Pulse Trains Generated Using the Temporal Talbot Effect", IEEE Photonics Technology Letters, vol. 18, No. 5, (Mar. 1, 2006), 3 pages.

Rasmussen, C. E. et al., "Gaussian Processes for Machine Learning", The MIT Press, Cambridge, Massachusetts, (2006), 266 pages.

Rasmussen, C. E. et al., "Gaussian Processes for Machine Learning (GPML) Toolbox", The Journal of Machine Learning Research, vol. 11, (2010), pp. 3011-3015.

Rasmussen, C. E. "Gaussian Processes in Machine Learning", L.N.A.I., vol. 3176, (2003) pp. 63-71.

(56) References Cited

OTHER PUBLICATIONS

Reinkensmeyer, D. et al., "Tools for understanding and optimizing robotic gait training," Journal of Rehabilitation Research & Development, vol. 43, No. 5, (Aug. 2006), 14 pages.
Rejc, E. et al., "Effects of Lumbosacral Spinal Cord Epidural Stimulation for Standing after Chronic Complete Paralysis in Humans," PLoS One, vol. 10, No. 7, (Jul. 24, 2015), 20 pages.
Robbins, H., "Some Aspects of the Sequential Design of Experiments", Bull. Amer. Math. Soc., vol. 58, (1952), pp. 527-535.
Rodger, D. C. et al., "High Density Flexible Parylene-Based Multielectrode Arrays for Retinal and Spinal Cord Stimulation", Proc. of the 14th International Conference on Solid-State Sensors, Actuators and Microsystems, (2007), pp. 1385-1888.
Rosenzweig, E. et al., "Extensive Spontaneous Plasticity of Corticospinal Projections After Primate Spinal Cord Injury", Nature Neuroscience, vol. 13, No. 12, Published Online Nov. 14, 2010, (Dec. 2010), 19 pages.
Ryzhov, I. O. et al., "The knowledge gradient algorithm for a general class of online learning problems", Operations Research, vol. 60, No. 1, (2012), pp. 180-195.
Sayenko, D. et al., "Neuromodulation of evoked muscle potentials induced by epidural spinal-cord stimulation in paralyzed individuals," Journal of Neurophysiology, vol. 111, No. 5, Published Online Dec. 11, 2013, (2014), 12 pages.
Shamir, R. R. et al., "Machine Learning Approach to Optimizing Combined Stimulation and Medication Therapies for Parkinson's Disease," Brain Stimulation, vol. 8, No. 6, Published Online Jun. 15, 2015, (Nov. 2015), 22 pages.
Srinivas, N. et al., "Gaussian process optimization in the bandit setting: No regret and experimental design", In Proceedings of the 27th International Conference on Machine Learning, (2010), 17 pages.
Steward, O. et al., "False Resurrections: Distinguishing Regenerated from Spared Axons in the Injured Central Nervous System", The Journal of Comparative Neurology, vol. 459, No. 1, (Apr. 21, 2003), 8 pages.
Stienen, A. H. A. et al., "Analysis of reflex modulation with a biologically realistic neural network," Journal of Computer Neuroscience, vol. 23, No. 3, Available Online May 15, 2007, (Dec. 2007), 16 pages.
Sun, F. et al., "Sustained axon regeneration induced by co-deletion of PTEN and SOCS3", Nature, vol. 480, No. 7377, Published Online Nov. 6, 2011, (Dec. 15, 2011), 12 pages.
Takeoka, A. et al., "Muscle Spindle Feedback Directs Locomotor Recovery and Circuit Reorganization after Spinal Cord Injury", Cell, vol. 159, No. 7, (Dec. 18, 2014), 27 pages.
Tenne, Y. et al., "Computational Intelligence in Expensive Optimization Problems", vol. 2 of Adaptation, Learning, and Optimization, Springer, Berlin Heidelberg, (2010), pp. 131-162.
Timozyk, W. et al., "Hindlimb loading determines stepping quantity and quality following spinal cord transection," Brain Research, vol. 1050, No. 1-2, Published Online Jun. 24, 2005, (Jul. 19, 2005), 10 pages.
Vallery, H. et al., "Compliant Actuation of Rehabilitation Robots," IEEE Robotics & Automation Magazine, vol. 15, No. 3, (Sep. 12, 2008), 10 pages.
Wan, D. et al., "Life-threatening outcomes associated with autonomic dysreflexia: A clinical review," Journal of Spinal Cord Medicine, vol. 37, No. 1, (Jan. 2014), 9 pages.
Ward, A. R., "Electrical Stimulation Using Kilohertz-Frequency Alternating Current", Physical Therapy, vol. 89, Published online Dec. 18, 2008, (2009), pp. 181-190.
Wenger, N. et al., "Supplementary Materials for Closed-loop neuromodulation of spinal sensorimotor circuits controls refined locomotion after complete spinal cord injury," Science Translational Medicine, vol. 6, No. 255, Sep. 24, 2014, 14 pages.
Wenger, N. et al., "Spatiotemporal neuromodulation therapies engaging muscle synergies improve motor control after spinal cord injury," Natural Medicine, vol. 22, No. 2, Feb. 2016, Available Online Jan. 18, 2016, 33 pages.
Wernig, A. et al., "Laufband locomotion with body weight support improved walking in persons with severe spinal cord injuries", Paraplegia, vol. 30, No. 4, (Apr. 1992), 10 pages.
Wernig, A., "Ineffectiveness of Automated Locomotor Training," Archives of Physical Medicine and Rehabilitation, vol. 86, No. 12, (Dec. 2005), 2 pages.
Wessels, M. et al., "Body Weight-Supported Gait Training for Restoration of Walking in People With an Incomplete Spinal Cord Injury: A Systematic Review," Journal of Rehabilitation Medicine, vol. 42, No. 6, (Jun. 2010), 7 pages.
Widmer, C. et al., Inferring latent task structure for multitask learning by multiple kernel learning, BMC Bioinformatics, vol. 11, (Suppl 8:S5), (2010), 8 pages.
Winter, D. A. et al., "An integrated EMG/biomechanical model of upper body balance and posture during human gait," Progress in Brain Research, vol. 97, Ch. 32, Available as Early as Jan. 1, 1993, (1993), 9 pages.
Wirz, M. et al., "Effectiveness of automated locomotor training in patients with acute incomplete spinal cord injury: A randomized controlled multicenter trial," BMC Neurology, vol. 11, No. 60, (May 27, 2011), 9 pages.
Yakovenko, S. et al., "Spatiotemporal Activation of Lumbosacral Motoneurons in the Locomotor Step Cycle," Journal of Neurophysiology, vol. 87, No. 3, (Mar. 2002), 12 pages.
Zhang, T. C. et al., "Mechanisms and models of spinal cord stimulation for the treatment of neuropathic pain," Brain Research, vol. 1569, Published Online May 4, 2014, (Jun. 20, 2014), 13 pages.
Zorner, B. et al., "Profiling locomotor recovery: comprehensive quantification of impairments after CNS damage in rodents," Nature Methods, vol. 7, No. 9, Published Online Aug. 15, 2010, (Sep. 2010), 11 pages.

* cited by examiner

NEUROMODULATION SYSTEM

CROSS REFERENCE TO RELATED APPLICATION

The present application claims priority to European Patent Application No. 19211698.6, entitled "NEUROMODULATION SYSTEM", and filed on Nov. 27, 2019. The entire contents of the above-listed application is hereby incorporated by reference for all purposes.

TECHNICAL FIELD

The present invention relates to a neuromodulation system, in particular a neuromodulation system for restoring motor function and/or autonomic function in a patient suffering from impaired motor and/or autonomic function after spinal cord injury (SCI) or neurologic disease.

BACKGROUND AND SUMMARY

Decades of research in physiology have demonstrated that the mammalian spinal cord embeds sensorimotor circuits that produce movement primitives (cf. Bizzi E. et al., *Modular organization of motor behavior in the frog's spinal cord. Trends in neurosciences* 18, 442-446 (1995); Levine A J. et al., *Identification of a cellular node for motor control pathways. Nature neuroscience* 17, 586-593 (2014)). These circuits process sensory information arising from the moving limbs and descending inputs originating from various brain regions in order to produce adaptive motor behaviors.

SCI interrupts the communication between the spinal cord and supraspinal centers, depriving these sensorimotor circuits from the excitatory and modulatory drives necessary to produce movement.

Epidural Electrical Stimulation (EES) of the spinal cord is a clinically accepted method for the treatment of chronic pain and has been approved by the Food and Drug Administration (FDA) since 1989 (Krames et al., 2009). Recently, several preclinical and clinical studies have demonstrated the use of EES applied to the lumbo-sacral levels of the spinal cord for the improvement of leg motor control after spinal cord injury. For example, EES has restored coordinated locomotion in animal models of SCI, and isolated leg movements in individuals with motor paralysis (cf. van den Brand R. et al., *Restoring Voluntary Control of Locomotion after Paralyzing Spinal Cord Injury. Science* 336, 1182-1185 (2012); Angeli C A. et al., *Altering spinal cord excitability enables voluntary movements after chronic complete paralysis in humans. Brain: a journal of neurology* 137, 1394-1409 (2014); Harkema S. et al., *Effect of epidural stimulation of the lumbosacral spinal cord on voluntary movement, standing, and assisted stepping after motor complete paraplegia: a case study. The Lancet* 377, 1938-1947 (2011); Danner S M. et al., *Human spinal locomotor control is based on flexibly organized burst generators. Brain: a journal of neurology* 138, 577-588 (2015); Courtine G. et al., *Transformation of nonfunctional spinal circuits into functional states after the loss of brain input. Nature neuroscience* 12, 1333-1342, (2009); Capogrosso M. et al., *A brain-spine interface alleviating gait deficits after spinal cord injury in primates. Nature* 539, 284-288, (2016)).

Moreover, EES can potentially be used for treatment of autonomic dysfunction (Harkema et al., 2018). Autonomic dysfunction may comprise altered and/or impaired regulation of at least one of blood pressure, heart rate, thermoregulation (body temperature), respiratory rate, immune system, gastro-intestinal tract (e.g. bowel function), metabolism, electrolyte balance, production of body fluids (e.g. saliva and/or sweat), pupillary response, bladder function, sphincter function and sexual function.

Moreover, EES can potentially be used for treatment of autonomic dysreflexia, spasticity, altered and/or impaired sleep behavior and/or pain.

EES as a neuromodulation strategy works—regardless of the application—by recruiting specific neuron populations through direct and indirect pathways. In the case of recovery of locomotion, EES applied over the lumbosacral spinal cord activates large-diameter, afferent fibers within the posterior roots which in turn activate motoneuron pools through synaptic connections, which in turn activate the muscles innervated by the corresponding neurons (Capogrosso M. et al., *A Computational Model for Epidural Electrical Stimulation of Spinal Sensorimotor Circuits. Journal of Neuroscience,* 33 (49) 19326-19340 (2013)). Hence, specific spinal roots are linked to specific motor functions (Sharrard W., *The segmental innervation of the lower limb muscles in man: Arris and gale lecture delivered at the royal college of surgeons of england on 2 Jan.* 1964. *Ann R Coll Surg Engl,* 35(2), 106-122 (1964)).

EP 3184145 A1 discloses systems for selective spatiotemporal electrical neurostimulation of the spinal cord. A signal processing device receiving signals from a subject and operating signal-processing algorithms to elaborate stimulation parameter settings is operatively connected with an Implantable Pulse Generator (IPG) receiving stimulation parameter settings from said signal processing device and able to simultaneously deliver independent current or voltage pulses to one or more multiple electrode arrays. The electrode arrays are operatively connected with one or more multi-electrode arrays suitable to cover at least a portion of the spinal cord of said subject for applying a selective spatiotemporal stimulation of the spinal circuits and/or dorsal roots, wherein the IPG is operatively connected with one or more multi-electrode arrays to provide a multipolar stimulation. Such system allows achieving effective control of locomotor functions in a subject in need thereof by stimulating the spinal cord, in particular the dorsal roots, with spatiotemporal selectivity.

In order to activate a muscle selectively a specific electric field needs to be generated within the spinal cord of a patient, dependent on the anatomical dimensions of that patient (Rattay F et al., *Epidural electrical stimulation of posterior structures of the human lumbosacral cord: 2. quantitative analysis by computer modeling. Spinal Cord,* 38, 473-489 (2000)). However, anatomical dimensions vary greatly between subjects. In order to increase efficacy and safety of the neuromodulation strategy the position and configuration of the stimulation paradigms should be known prior to the surgical implantation of the spinal cord implant.

US 2018104479 A1 discloses systems, methods, and devices for optimizing patient-specific stimulation parameters for spinal cord stimulation, in order to treat pain. A patient-specific anatomical model is developed based on pre-operative images, and a patient-specific electrical model is developed based on the anatomical model. The inputs to the electric model are chosen, and the model is used to calculate a distribution of electrical potentials within the modeled domain. Models of neural elements are stimulated with the electric potentials and used to determine which elements are directly activated by the stimulus. Information about the models inputs and which neural elements are active is applied to a cost function. Based on the value of the cost function, the inputs to the optimization process may be adjusted. Inputs to the optimization process include lead/electrode array geometry, lead configuration, lead positions, and lead signal characteristics, such as pulse width, amplitude, frequency and polarity.

It is an object of the present invention to enable optimal placement of a spinal implant, e.g. a lead comprising multiple electrodes, in a patient suffering from impaired motor and/or autonomic function after SCI or neurologic disease.

This object is solved according to the present invention by a neuromodulation system with the features of claim 1. Accordingly, a neuromodulation system comprising
- at least one input module for inputting patient data into the neuromodulation system;
- at least one model calculation and building module for building a patient model, the patient model describing an anatomy and/or physiology and/or pathophysiology and a real and/or simulated reaction of the patient on a provided and/or simulated neuromodulation;
- at least one computation module for using the patient model and calculating the impact of the provided and/or simulated neuromodulation.

The invention is based on the basic idea that a multi-layer computational framework for the design and personalization of stimulation protocols, in particular EES protocols, for neuromodulation purposes for a patient should be provided in order to enable patient-specific neuromodulation. The use of a general concept including at least one input module, at least one model calculation and building module and at least one computation module may provide a pipeline combining image thresholding and Kalman-filtering and/or specific algorithms for at least partially automatically reconstructing the patient's anatomy, such as the spinal cord, the vertebrae, the epidural fat, the pia mater, the dura mater, the posterior roots or dorsal roots, the anterior roots or ventral roots, the rootlets, the cerebro-spinal fluid (CSF), the white matter, the grey matter and/or the intervertebral discs from a dataset obtained by an imaging method. A computational pipeline to automatically create 2D and/or 3D models, e.g. 3D Finite Element Method models (FEM), from these reconstructions is established, to obtain anisotropic tissue property maps, discretize the model, perform simulations using an electro-quasi-static solver and couple these simulations with electrophysiology models, in particular neuron-based and/or nerve fiber based electrophysiology models, of the spinal cord and/or dorsal roots. Overall, patient-specific neuromodulation, specifically adapted to the patient's needs and anatomy, may be enabled.

The system may be used in a method for the treatment of motor impairment and/or restoring motor function. Motor function may comprise all voluntary postures and movement patterns, such as locomotion.

The system may be used in a method for the treatment of autonomic dysfunction and/or restoring autonomic function. Autonomic dysfunction may comprise altered and/or impaired regulation of at least one of blood pressure, heart rate, thermoregulation (body temperature), respiratory rate, immune system, gastro-intestinal tract (e.g. bowel function), metabolism, electrolyte balance, production of body fluids (e.g. saliva and/or sweat), pupillary response, bladder function, sphincter function and sexual function.

The system may be used in a method for the treatment of autonomic dysreflexia, spasticity, altered and/or impaired sleep behavior and/or pain.

In particular, the system may also be used for a neuromodulation system in a decoupled manner to set a neuromodulation system based on patient data and/or feedback information, e.g. as a generic system decoupled from an implanted neuromodulation system.

In particular, the system may enable to describe the patient's anatomy in detail, in terms of every tissue in the spinal cord including crucial trajectories of the spinal roots (dorsal and/or ventral roots), enabling to fully segment out all tissues including the spinal roots for an individual patient and to implement spinal rootlets to fit the geometrical area between the entry point of one spinal root versus the next.

In particular, a computational pipeline to automatically create anisotropic tissue property maps in the 3D reconstruction and overlay them as conductivity maps over the 3D FEM model may be provided.

In particular, the system may establish a computational pipeline to automatically create topologically and neuro-functionally realistic compartmental cable models within the personalized 3D FEM models, including but not limited to, A$\alpha$-, A$\beta$-, A$\delta$-, C-sensory fibers, interneurons, $\alpha$-motoneurons and efferent nerves, as well as dorsal column projections.

The system may enable to determine optimal stimulation parameters (such as frequency, amplitude and/or pulse width and/or polarity) and/or optimal electrode configuration for the specific recruitment of A$\alpha$ nerve fibers of at least one dorsal root. In particular, the system may enable to determine optimal stimulation parameters and/or optimal electrode configuration for the specific recruitment of A$\alpha$ nerve fibers but not all fibers of at least one dorsal root. In particular, the system may enable to determine optimal stimulation parameters and/or optimal electrode configuration for the specific recruitment of A$\alpha$ nerve fibers but not of A$\beta$ nerve fibers and/or A$\delta$ nerve fibers and/or C nerve fibers of the at least one dorsal root. In particular, the system may enable to determine optimal stimulation parameters (such as frequency, amplitude and/or pulse width, and/or polarity) and/or optimal electrode configuration for the specific recruitment of A$\alpha$ nerve fibers in at least one dorsal root but not A$\beta$ nerve fibers in the dorsal column. This may enable to optimize patient treatment for elicitation of motor responses. In other words, this may enable that a patient suffering from SCI and/or motor dysfunction is successfully treated with neuromodulation to restore motor function. Alternatively, and/or additionally, autonomic function may be restored.

In particular, a cost function for optimizing lead position may be used to determine a selectivity index. For example, the selectivity index may be calculated through a distance function:

$$\text{dist}(j)=\text{sqrt}[(\text{sum}\_i(w\_i*(x\_\text{desired}\_i(j)-x\_\text{achieved}\_i(j))))**2]$$

with x being the percentage of a specific type of nerve fiber being activated within one dorsal root and i being a combination of dorsal roots and neve fiber types that have been initialized and j being the current used;
- Reiterate the selectivity index for a multitude of different lead positions;
- Find the minimal distance among all lead positions;
- Take the dist(j) function for that position for all possible active sites;
- Minimize it through superposition of the active sites to calculate the multipolar configuration.

In particular, the system may establish a pipeline to couple the results of a previous calculation to the compartmental cable models to calculate the depolarization of individual nerve fibers and/or neurons as well as the travelling of action potentials. In particular, the electrophysiological response may be validated in personalized models created through this pipeline against their real-life counterparts. In particular, this may enable to decode the mechanisms of neuromodulation as well as explore neural circuitry, especially specifically for a person with spinal cord injury and/or injury of nerve fibers (also referred to as a patient).

In particular, this framework may be used to determine the optimal placement of a spinal implant, such as a lead and/or an electrode array, in an individual subject prior to the actual surgery. Additionally, and/or alternatively, a genetic algorithm may automatically determine the optimal stimulation paradigms for recruiting a nerve fiber and/or neuron population within the spinal cord of the subject.

EES may be utilized for enabling motor functions by recruiting large-diameter afferent nerve fibers within the posterior roots. Electrode positioning and/or stimulation configuration may have an immense effect on the selectivity of this recruitment pattern and is dependent on the anatomy of each subject. Currently these parameters can only be determined by time-consuming, invasive and often unsuccessful trial and error procedures. In particular, the system may enable optimization of electrode position and/or stimulation configuration for enabling optimal motor function as the computational pipeline of the system enables that these parameters can be determined automatically and non-invasively for each subject and/or patient.

Similarly, EES may affect the autonomic nervous system through activation of specific spinal roots. The determination of electrode position and/or a stimulation protocol follows the same logic as for motor function but with a different goal. In particular, the system may enable optimization of electrode position and stimulation configuration for the treatment of autonomic dysfunction.

In particular, the system may enable developing novel electrode arrays and/or leads and/or optimization of novel electrode designs for neuromodulation therapies, in particular for patient specific neuromodulation therapies. In general, it may be possible that the system enables to assess, prior to surgery, which lead (of a lead portfolio with different sizes/electrode configurations) is most suitable for an individual patient. In particular, for any neuromodulation strategy an electrode and/or electrode array and/or lead needs to be designed or selected. Currently the optimization procedure depends primarily on experience and extensive testing in animal models and humans. This is an expensive, time-consuming, ineffective and partially unsafe undertaking. The system may enable that a virtual population of personalized computational models may be created from imaging datasets to optimize the electrode and/or electrode array and/or lead design in-silico, before testing safety and efficacy in-vivo. In particular, this may also enable to reduce the number of animals required for animal studies.

In particular, the input module may be configured and arranged for reading imaging datasets, e.g. from MRI, CT, Fluoroimaging, X-Ray, IR, video, laser measuring, optical visualization and/or other imaging systems, real-time registration, navigation system imaging, EEG, ECG, EMG, mechanical feedback and the like.

In particular, imaging datasets may be or may comprise high-resolution imaging datasets on individual subjects and/or patients. In particular, high-resolution imaging datasets may be obtained by high-resolution imaging machines that have the capacity to reveal the complete anatomy of the spinal cord, the vertebrae, the epidural fat, the pia mater, the dura mater, the posterior roots/dorsal roots, the anterior roots/ventral roots, the rootlets, the white matter, the grey matter, the intervertebral discs and/or the CSF of individual patients.

The input module may enable that a user, e.g. a therapist, a physiotherapist, a physician, a trainer, a medical professional and/or a patient directly provides patient data. In particular, the input module may be or may comprise a user interface of an input device.

In particular, the system may further comprise output device, such as a display unit, for outputting at least one of pre-operative planning data, intra-operative planning data and/or post-operative planning data. In particular, the output device may provide visual information on the pre-operative planning data, intra-operative planning data and/or post-operative planning data. In particular, this may enable that a user, e.g. a surgeon and/or therapist, is provided with exact anatomical and/or physiological and/or pathophysiological data of an injured person and may select optimal neuromodulation therapy configurations.

In particular, pre-operative planning data may include at least one of surgical incision placement, optimal electrode placement, eligibility of the patient, in-silico assessment of benefit for decision making. In particular, this has the advantage that optimal stimulation, specifically adapted to a patient's needs is enabled and/or surgery procedures are kept as short as possible, without harming the patient by unnecessary trial-and error procedures.

The intra-operative planning data may include at least one intra-operative imaging data such as MRI, CT, Fluoroimaging, X-Ray, IR, video, laser measuring, optical visualization and imaging, real-time registration, navigation system imaging, EEG, ECG, EMG, mechanical feedback and the like. This has the advantage that the patient's anatomy including any injured tissue and/or anatomical peculiarities and/or physiology and/or pathophysiology is revealed, and the planned therapy can be adapted specifically to the patient's needs.

In particular, the post-operative planning data may include at least one recommend optimum electrode configuration, stimulation waveforms, timings schedule for neuromodulation events and the like. This may enable that the neuromodulation and/or neuromodulation therapy may be adapted to specific tasks and, at the same time, to the patient's needs. Overall, this may enable optimal neuromodulation outcome.

In particular the output device may provide visualization of at least one of electric currents, potentials, information on the location and/or probability of the depolarization of nerve fibers and/or neurons. In particular, this may be referred to as neurofunctionalization, enabling visualization of excitation of target nerves in order to better understand neuromodulation and/or neuromodulation therapy.

In particular, the system may be used for percutaneous electrical stimulation, transcutaneous electrical nerve stimulation (TENS), epidural electrical stimulation (EES), subdural electrical stimulation (SES), functional electrical stimulation (FES) and/or all neurostimulation and/or muscle stimulation applications.

Further, the system may additionally comprise at least one of a sensor, a sensor network, a controller, a programmer, a telemetry module, a communication module, a stimulator, e.g. an implantable pulse generator and/or a lead comprising an electrode array comprising at least one electrode (up to multiple electrodes).

Alternatively and/or additionally, the system may be connected to a system comprising at least one of a sensor, a sensor network, a controller, a programmer, a telemetry module, a communication module, a stimulator, e.g. an implantable pulse generator, a lead comprising multiple electrodes and/or a memory, wherein stimulation parameters and/or electrode configuration and/or tasks may be stored in the memory and the patient may start training without any post-operative functional mapping.

Further, the system may be comprised in a browser and/or cloud and/or a desktop computer.

The system may be a closed-loop system or an open-loop system.

It is also possible that the system allows both closed-loop and open loop functionality. In this regard, the user may switch between these options or there may be routines or control elements that can do or propose such a switch from closed-loop to open-loop and vice versa.

According to the present invention a method is disclosed, the method characterized in that the method is performed with the system of any of claims 1-6.

In particular, the method may be a method for providing neuromodulation, the method comprising at least the steps of:
  inputting patient data;
  building a patient model, the patient model describing the anatomy and/or physiology and/or pathophysiology and the real and/or simulated reaction of the patient on a provided and/or simulated neuromodulation;
  calculating the impact of the provided and/or simulated neuromodulation.

In particular the method may further comprise the step of outputting at least one of pre-operative planning data, intra-operative planning data and/or post-operative planning data.

In particular, the method may be characterized in that visualization, e.g. 3D visualization, of at least one of electric currents, potentials, information on the location and/or probability of the depolarization of nerve fibers and/or neurons are provided.

BRIEF DESCRIPTION OF THE FIGURES

Further details and advantages of the present invention shall now be disclosed in connection with the drawings.

DETAILED DESCRIPTION

Figure 1:
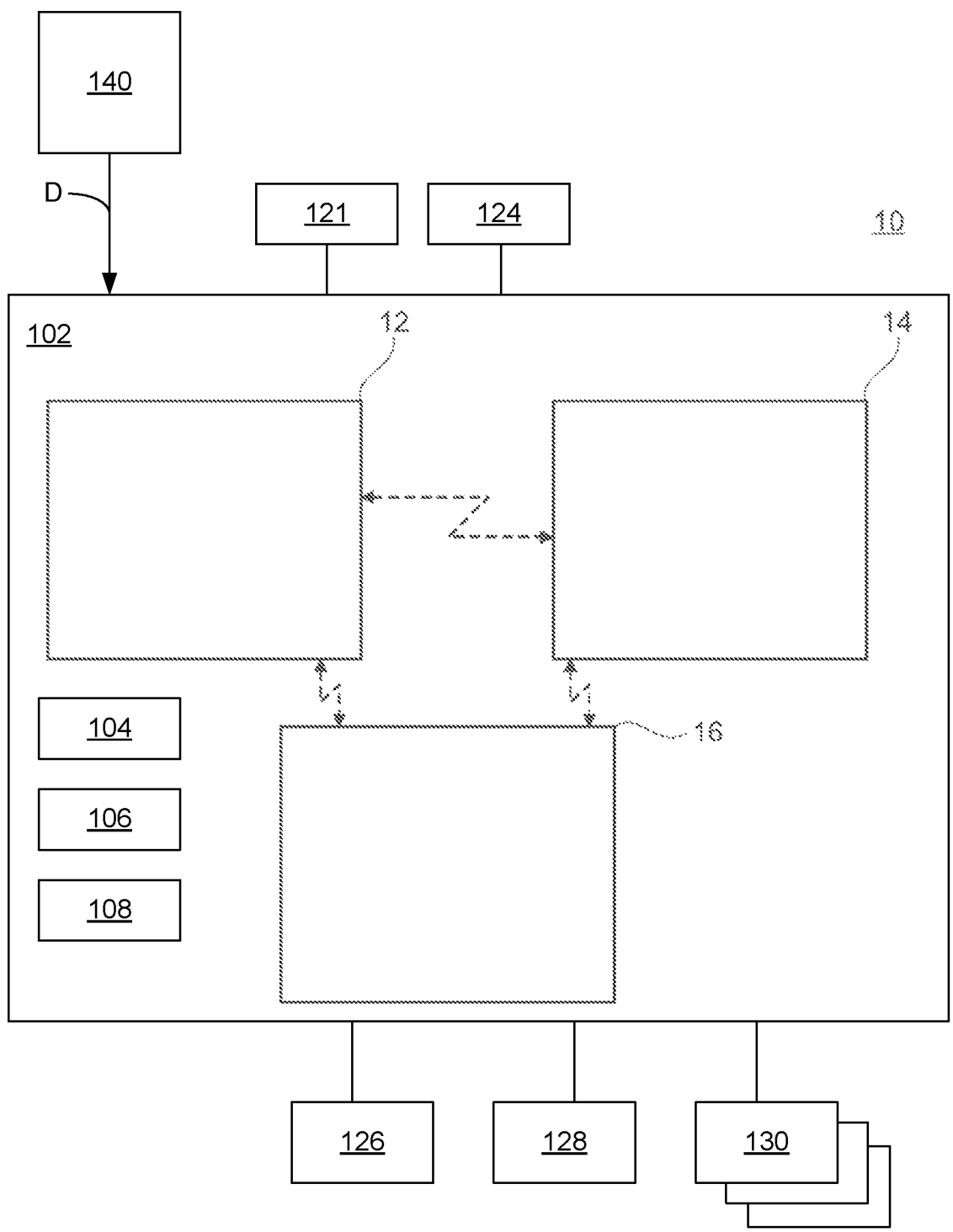
FIG. 1 shows a schematic overview of an embodiment of the neuromodulation system according to the present invention, with which the method according to the present invention may be performed.

FIG. 1 shows a schematic overview of an embodiment of the neuromodulation system 10 according to the present invention, with which the method according to the present invention may be performed. The system 10 may include a device 102 with an input module 112, a model calculation and building module 14, a computation module 16, a memory 104, a processor 106, and a communication subsystem 108, though other components and modules may also be included as known to those of skill in the art including, but not limited to, a controller, a microcontroller, a telemetry system and/or a training device. Further, additionally or alternatively, one or more of the input module 12, the model calculation and building module 14, and the computation module 16 may include one or more processors, such as processor 106, and memory, such as memory 106.

In some aspects, as shown in FIG. 1, the device 102 may be coupled to a user input device 121, an output device 124, an electrode array 126 comprising one or more electrodes, a pulse generator 128, and one or more sensors 130. In one example, the output device may be a display screen, or a portion of a display screen. While the device 102 is shown with a plurality of peripheral devices, the particular arrangement may be altered by those of skill in the art such that some or all of the components are incorporated in a single or plurality of devices as desired.

Collectively, the various tangible components or a subset of the tangible components of the neuromodulation system may be referred to herein as "logic" configured or adapted in a particular way, for example as logic configured or adapted with particular software, hardware, or firmware and adapted to execute computer readable instructions. The processors may be single core or multicore, and the programs executed thereon may be configured for parallel or distributed processing. The processors may optionally include individual components that are distributed throughout two or more devices, which may be remotely located and/or configured for coordinated processing. One or more aspects of the logic subsystem may be virtualized and executed by remotely accessible networked computing devices configured in a cloud computing configuration, that is, one or more aspects may utilize ubiquitous, convenient, on-demand network access to a shared pool of configurable computing resources that can be rapidly provisioned and released with minimal management effort or service provider interaction. Clouds can be private, public, or a hybrid of private and public, and may include Infrastructure as a Service (IaaS), Platform as a Service (PaaS) and Software as a Service (SaaS). In some aspects, logic and memory may be integrated into one or more common devices, such as an application specific integrated circuit, field programmable gate array, or a system on a chip.

In some embodiments, device 102 may be any computing or mobile device, for example, mobile devices, tablets, laptops, desktops, PDAs, and the like, as well as virtual reality devices or augmented reality devices. Thus, in some embodiments, the device 102 may include an output device, and thus a separate output device 124 or user input device 121 may not be necessary. In other aspects, the device may be coupled to a plurality of displays.

Memory 104 generally comprises a random-access memory ("RAM") and permanent non-transitory mass storage device, such as a hard disk drive or solid-state drive. Memory 104 may store an operating system as well as the various modules and components discussed herein. It may further include devices which are one or more of volatile, non-volatile, dynamic, static, read/write, read-only, random access, sequential access, location addressable, file addressable and content addressable.

Communication subsystem 108 may be configured to communicatively couple the modules within device 102 as well as communicatively coupling device 102 with one or more other computing and/or peripheral devices. Such connections may include wired and/or wireless communication devices compatible with one or more different communication protocols including, but not limited to, the Internet, a personal area network, a local area network (LAN), a wide area network (WAN) or a wireless local area network (WLAN). For example, wireless connections may be WiFi, Bluetooth®, IEEE 802.11, and the like.

As shown in FIG. 1,

The system 10 comprises an input module 12.

The input module 12 is configured for inputting patient data D into the neuromodulation system 10. In one example, patient data D may be acquired via a patient data acquisition modality 140, which may be one of MRI, CT, Fluoroimaging, X-Ray, IR, video, laser measuring, optical visualization and imaging means, real-time registration, navigation system imaging, EEG, ECG, EMG, mechanical feedback and the like.

Alternatively, the system 10 could comprise more than one input module 12.

The system 10 further comprises a model calculation and building module 14.

The model calculation and building module 14 is configured for building a patient model M, the patient model M describing the anatomy and/or physiology and/or pathophysiology and the real and/or simulated reaction of the patient on a provided and/or simulated neuromodulation. For example, the model calculation and building module 14 may generate the patient model M according to patient data D input via the input module 12.

Alternatively, the system 10 could comprise more than one model calculation and building module 14.

The system 10 further comprises a computation module 16.

The computation module 16 is configured for using the patient model M and calculating an impact of a provided and/or simulated neuromodulation. In one example, calculating the impact may be include calculating one or more neurofunctionalization parameters including but not limited to one or more of electric currents, potentials, information on the location and/or probability of the depolarization of nerve fibers and/or neurons. The one or more neurofunctionalization parameters may enable visualization of excitation of target nerves in order to better understand neuromodulation and/or neuromodulation therapy.

Alternatively, the system 10 could comprise more than one computation module 16.

In this embodiment, the input module 12 is connected to the model calculation and building module 14.

The connection between the input module 12 and the model calculation and building module 14 is a direct and bidirectional connection.

However, in an alternative embodiment, an indirect and/or unidirectional connection could be generally possible.

In this embodiment, the connection between the input module 12 and the model calculation and building module 14 is a wireless connection.

However, in an alternative embodiment, a cable-bound connection could be generally possible.

In this embodiment, the input module 12 is connected to computation module 16.

The connection between the input module 12 and the computation module 16 is a direct and bidirectional connection.

However, in an alternative embodiment, an indirect and/or unidirectional connection could be generally possible.

In this embodiment, the connection between the input module 12 and the computation module 16 is a wireless connection.

However, in an alternative embodiment, a cable-bound connection could be generally possible.

In this embodiment, the model calculation and building module 14 is connected to computation module 16.

The connection between the model calculation and building module 14 and the computation module 16 is a direct and bidirectional connection.

However, in an alternative embodiment, an indirect and/or unidirectional connection could be generally possible.

In this embodiment, the connection between the model calculation and building module 14 and the computation module 16 is a wireless connection.

However, in an alternative embodiment, a cable-bound connection could be generally possible.

In this embodiment, the input module 12 inputs patient data D on the anatomy and/or physiology and/or pathophysiology of a patient into the system 10.

In other words, the input module 12 reads patient data D.

In this embodiment, the patient is a patient suffering from SCI.

In this embodiment, the patient is a patient suffering from motor dysfunction.

In an alternative embodiment, the patient could be a patient suffering from impaired motor dysfunction and/or impaired autonomic function.

In this embodiment, patient data D are obtained by one of MRI, CT, Fluoroimaging, X-Ray, IR, video, laser measuring, optical visualization and imaging means, real-time registration, navigation system imaging, EEG, ECG, EMG, mechanical feedback and the like.

In this embodiment, the model calculation and building module 14 builds, based on the patient data D provided by the input module 12, a patient model M.

In this embodiment, the patient model M describes the anatomy of the patient and the real reaction of the patient on provided neuromodulation.

Alternatively, and/or additionally, the patient model M could describe the physiology and/or pathophysiology and the simulated reaction of the patient on provided and/or simulated neuromodulation.

In this embodiment, the computation module 16 uses the model M and calculates the impact of the provided neuromodulation.

Not shown in FIG. 1 is that the system 10 may further comprise an output device for outputting at least one of pre-operative planning data, intra-operative planning data and/or post-operative planning data. Additionally or alternatively, the one or more of pre-operative planning data, intra-operative planning data and post-operative planning data may be output via the output device 124 coupled to the system 10, as shown in FIG. 1.

Figure 4:
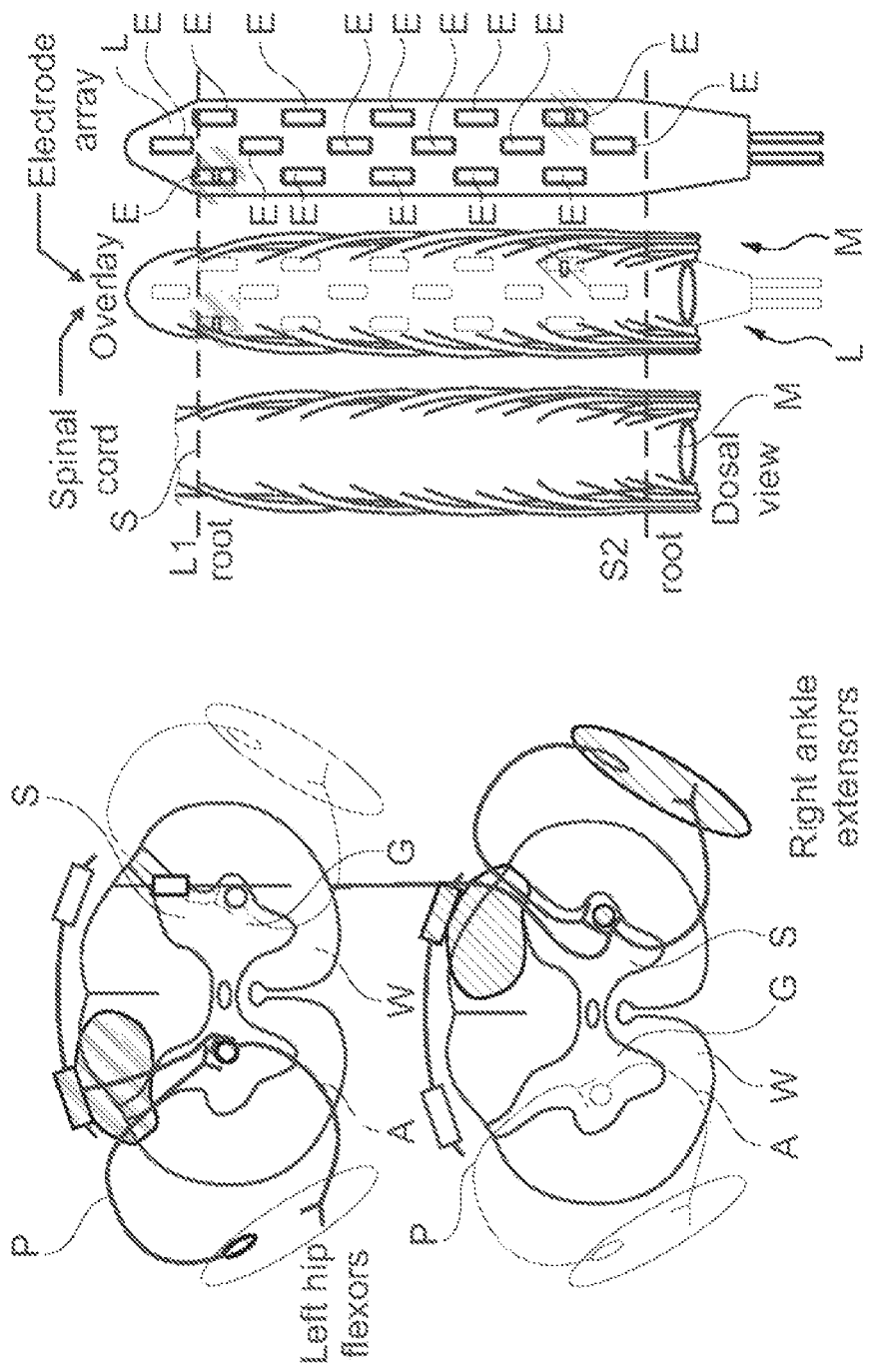
FIG. 4 shows an example of optimization of electrode position and stimulation configuration with the system disclosed in FIG. 1.

Not shown in FIG. 1 is that the pre-operative planning data could include at least one of surgical incision placement, optimal electrode E placement, eligibility of the patient, assessment of in-silico benefit for decision making, cf. FIG. 4.

Figure 2:
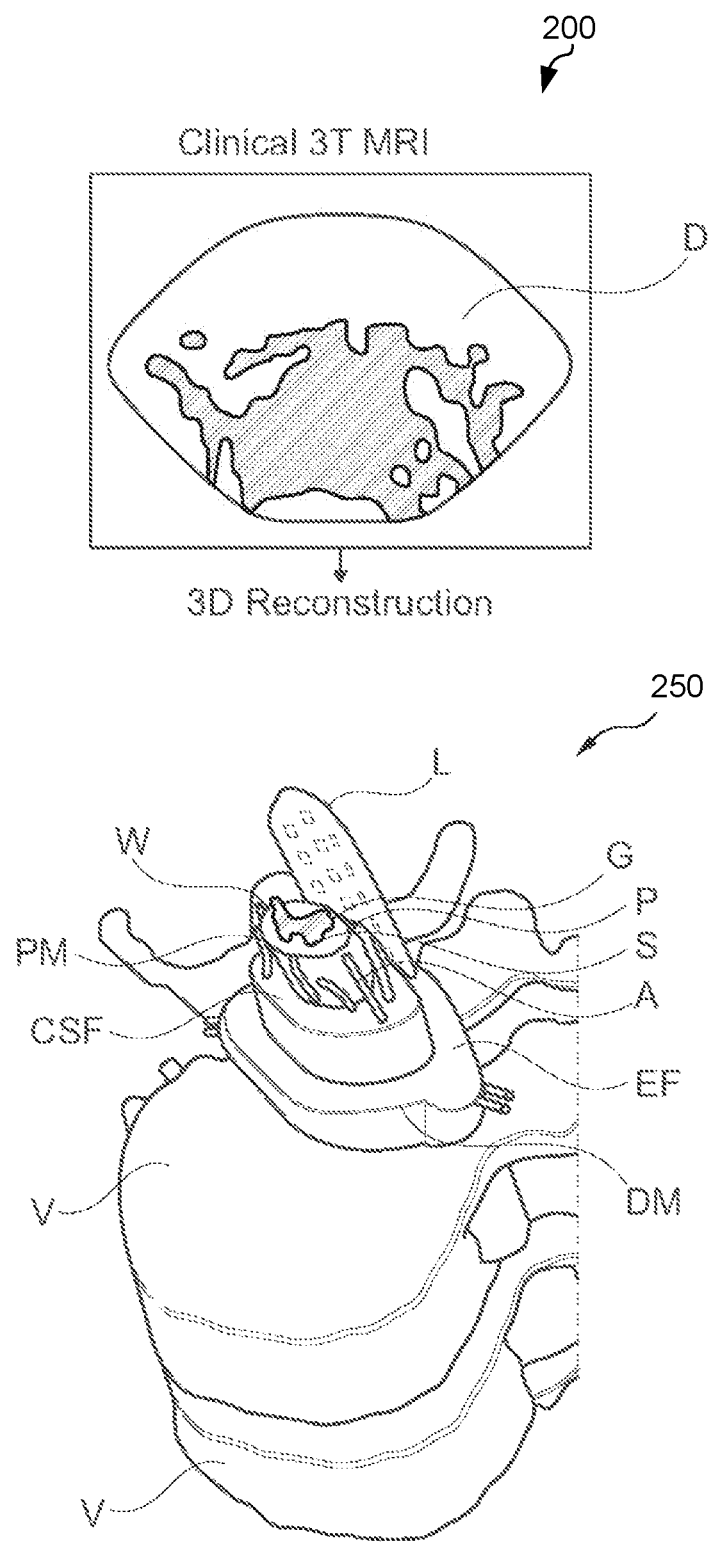
FIG. 2 shows an example of a patient model build from patient data by the model calculation and building module, according to the present invention as disclosed in FIG. 1.
Figure 3:
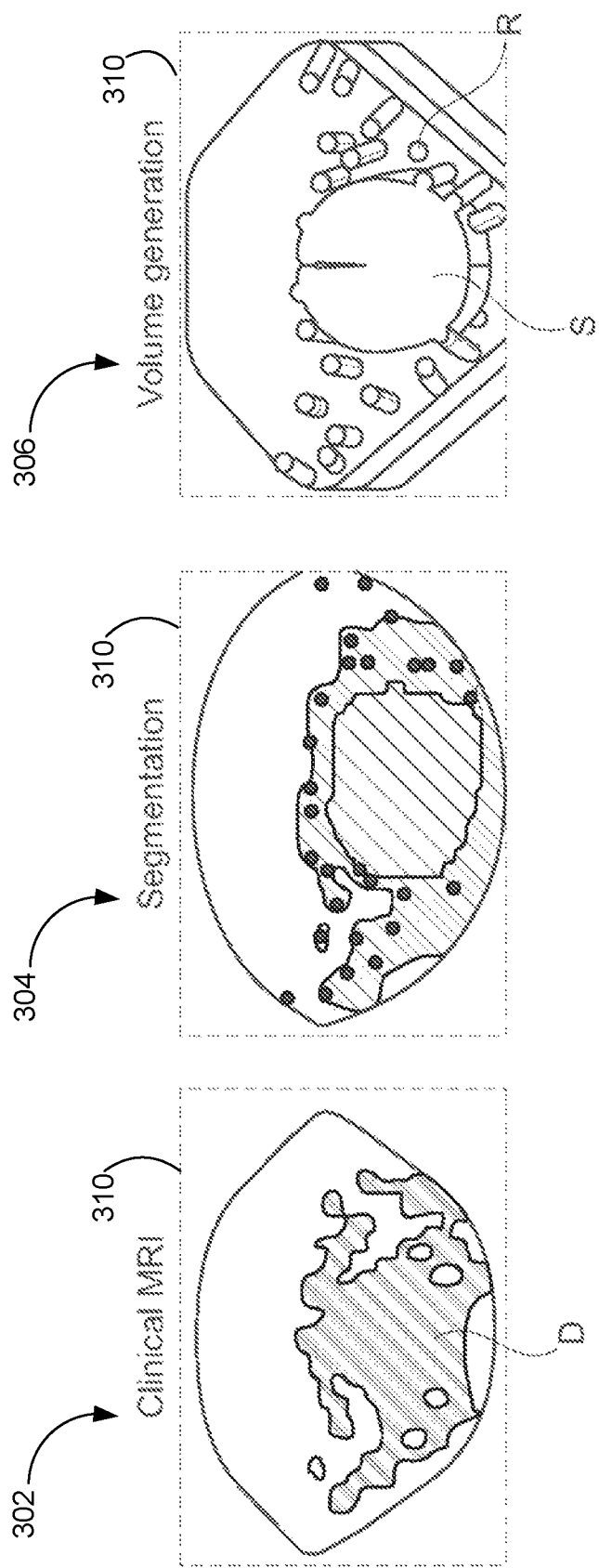
FIG. 3 shows an example of how a patient model as shown in FIG. 2 is built from patient data by the model calculation and building module, according to the present invention as disclosed in FIG. 1.

Not shown in FIG. 1 is that the intra-operative planning data could include at least one intra-operative imaging data such as MRI, CT, Fluoroimaging, X-Ray, IR, video, laser measuring, optical visualization and imaging module, real-time registration, navigation system imaging, EEG, ECG, EMG, mechanical feedback and the like, cf. FIGS. 2 and 3.

Not shown in FIG. 1 is that the post-operative planning data could include at least one recommend optimum electrode E configuration, electrode E design, plan, stimulation waveforms, timings schedule for neuromodulation events and the like.

Figure 5:
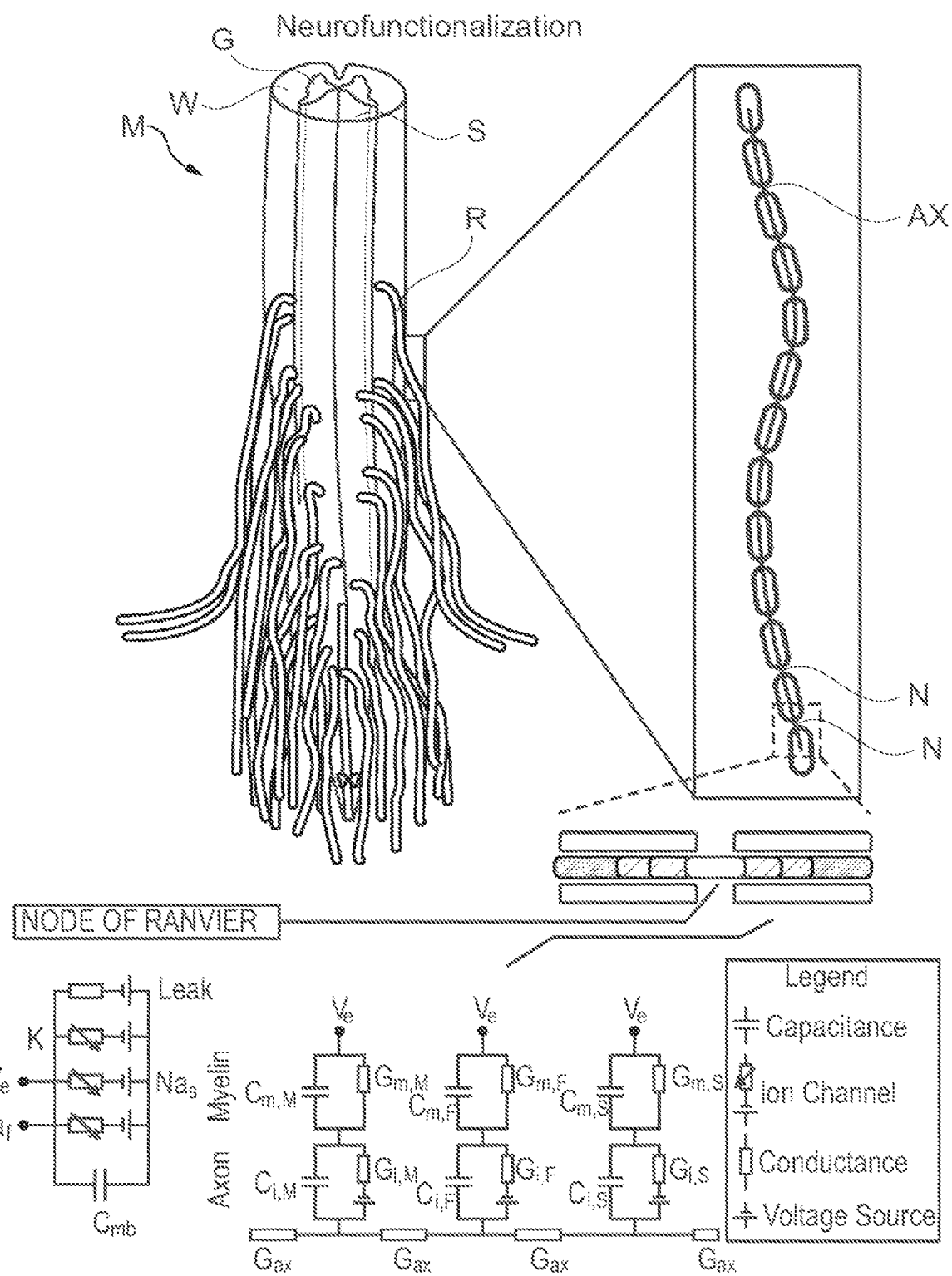
FIG. 5 shows an example of neurofunctionalization with the system disclosed in FIG. 1.

Not shown in FIG. 1 is that the output device could provide visualization, e.g. 3D visualization, of at least one of electric currents, potentials, information on the location and/or probability of the depolarization of nerve fibers and/or neurons, cf. FIG. 5.

Not shown in FIG. 1 is that the system 10 is a system for restoring motor and/or autonomic function in a patient.

Not shown in FIG. 1 is that the system could enable to determine optimal stimulation parameters (such as frequency, amplitude and/or pulse width) for the specific recruitment of Act nerve fibers of at least one dorsal root.

In general, one or more processors of the system 10 may include executable instructions in non-transitory memory that when executed may perform a method for providing neuromodulation, the method comprising at least the steps of:
  inputting patient data D;
  building a patient model M, the patient model M describing the anatomy and/or physiology and/or pathophysiology and the real and/or simulated reaction of the patient on provided and/or simulated neuromodulation;
  calculating the impact of the provided and/or simulated neuromodulation.

The method could further comprise the step of outputting at least one of pre-operative planning data, intra-operative planning data and/or post-operative planning data.

The method could further comprise the step of providing visualization of at least one of electric currents, potentials, information on the location and/or probability of the depolarization of nerve fibers and/or neurons are provided.

FIG. 2 shows an example of a patient model 250 (e.g., patient model M described above with respect to FIG. 1) built by the model calculation and building module 14 according to the present invention as disclosed in FIG. 1. The patient model 250 may be generated by using patient data D from an imaging scan 200 acquired via a modality, such as clinical 3T MRI modality.

In this embodiment, the model calculation and building module 14 of the system 10 disclosed in FIG. 1 builds a patient model 250 describing the anatomy of a patient.

In this embodiment, the system 10 further comprises an output device for outputting intra-operative planning data.

In this embodiment, the output device is connected to the input module 12, the model calculation and building module 14 and the computation module 16 of the system 10 via a wireless connection.

In this embodiment, the connection is a wireless connection and bidirectional connection.

However, in an alternative embodiment, a wired (e.g., a cable-bound) and/or unidirectional connection could be generally possible.

In an alternative embodiment, the output device could be connected to only one or at least one of to the input module 12, the model calculation and building module 14 and the computation module 16 of the system 10.

In this embodiment, the model calculation and building module 14 builds a patient model 250 based on patient data D.

In this embodiment, the patient data D is intra-operative planning data.

In this embodiment, the patient data D is imaging data obtained by a 3T MRI scanner. In some embodiments, the patient data D is imaging data obtained by an MRI scanner.

In this embodiment, the patient model 250 is a 3D reconstruction of the patient data 200.

In other words, the patient model 250 is a 3D reconstruction of the MRI scan.

In this embodiment, the output device provides visual information via a display.

In other words, the shown embodiment is, at least partly, visual information provided by the output device.

In this embodiment, the output device provides the patient model 250 built by the model calculation and building module 14.

In an alternative embodiment, the patient model 250 could be or could comprise a 2D reconstruction of the patient data D.

In this embodiment the patient model 250 comprises a 3D reconstruction of the spinal cord S, vertebrates V, epidural fat EF, pia mater PM, dura mater DM, dorsal roots P, ventral roots A, cerebro-spinal fluid CSF, the white matter W and the grey matter G of a patient.

In this embodiment, the patient model 250 is combined with a model of a lead L comprising multiple electrodes for providing neuromodulation.

Not shown in this embodiment is that the computation module 16 uses the patient model 250 and calculates the impact of the neuromodulation provided by the lead L.

Not shown in this embodiment is that, via a user interface of the output device, a user could edit the patient model 250, e.g. by zooming in and/or zooming out and/or rotating and/or adding and/or changing colors.

FIG. 3 schematically shows an example of how a patient model, such as patient model 250 as shown in FIG. 2 is built from patient data D by a model calculation and building module of a system, such as the model calculation and building module 14 of system 10 according to the present invention as disclosed in FIG. 1. In the present example, the patient data D acquired via a clinical MRI scan is shown at 302. The model calculation and building module may then employ a segmentation algorithm to generate a segmented image 304 using the patient data D. Upon segmentation, a model 306, may be generated by the model calculation and building module. The model 306 is depicted as a 3D model; it will be appreciated that other types of models may be generated using patient data D.

In this embodiment, the system further comprises an output device for outputting patient data D, which may include intra-operative planning data. In one example, the patient data D may be output via a display portion 310 of the output device.

In this embodiment, the output device is connected to an input module, such as the input module 12, the model calculation and building module and a computation module, such as computation module 16 of the system 10 via a wireless connection, cf. FIG. 1.

In this embodiment, the intra-operative planning data is an MRI image.

In this embodiment, the output device provide visual information via a display portion 310 of a display. In some examples, the patient data D (that is, MRI image in this example) shown at 302, the segmented image 304, and the model 306 may be displayed adjacent to each other on the display. Alternatively, the display may output a user-selected image (e.g., user may select a desired image and/or data to view via the display).

In this embodiment, the output device provide the patient model 306 build by the model calculation and building module 14. Another example patient model M is shown at FIG. 2.

Not shown in FIG. 3 is that in general, the system enables semi-automatic reconstruction of patient's anatomy, such as the spinal cord S, the vertebrae V, the epidural fat EF, the pia mater PM, the dura mater DM, the posterior roots or dorsal roots P, the anterior roots or ventral roots A, the rootlets R, the cerebro-spinal fluid CSF, the white matter W, the grey matter G, the intervertebral discs I, based on image thresholding and/or Kalman-filtering and/or various algorithms.

Not shown in FIG. 3 is that in generally, a computational pipeline could be established by the system 10 to automatically create 2D and/or 3D models, e.g. 3D Finite Element Method models (FEM), from these reconstructions, to obtain anisotropic tissue property maps, discretize the model, perform simulations using an electro-quasi-static solver and couple these simulations with electrophysiology models of the spinal cord and/or dorsal roots.

In this embodiment, the system, via model 306, describes a patient's anatomy in terms of every tissue in the spinal cord S area.

In this embodiment, the system, via model 306, describes a patient's anatomy in terms of a volume of every tissue in the spinal cord S area.

In this embodiment, the system, via model 306, describes the patient's anatomy in terms of every tissue in the spinal cord S area, including crucial trajectories of the spinal roots R, enabling to segment out all tissues including the spinal roots R for an individual patient and to implement spinal rootlets to fit the geometrical area between the entry point of one root versus the next.

FIG. 4 shows an example of optimization of electrode E position and stimulation configuration with the system 10 disclosed in FIG. 1.

In this embodiment, the system 10 disclosed in FIG. 1 further comprises output device for outputting pre-operative planning data, cf. FIGS. 2, 3.

In this embodiment, the output device provide visual information via a display.

In other words, the shown embodiment is, at least partly, visual information provided by the output device.

In general, the output device may comprise a user interface, enabling the user to change pre-operative planning data.

In this embodiment, the pre-operative planning data comprise optimal electrode E placement.

In other words, the system 10 enables optimal placement of a lead L comprising multiple electrodes E.

In this embodiment a lead L comprising multiple electrodes E is superimposed on a patient model M.

In general, EES can be utilized for enabling motor functions by recruiting large-diameter afferent nerve fibers within the dorsal roots P.

Electrode E positioning and stimulation configuration has an immense effect on the selectivity of this recruitment pattern and is dependent on the anatomy of each subject.

In this embodiment, the system 10 disclosed in FIG. 1 is used for optimization of electrode E position and stimulation configuration for enabling motor function.

In this embodiment, left hip flexors and right ankle extensors should be stimulated with a lead L comprising multiple electrodes E.

In this embodiment, L1 and S2 dorsal roots should be stimulated by electrodes E of the lead L In particular, the cost function could be:

Calculate the selectivity through a distance function $$\text{dist}(j) = \text{sqrt}[(\text{sum}\_i(w\_i^*(x\_\text{desired}\_i(j) - x\_\text{achieved}\_i(j))))^{**}2]$$

with x being the percentage of a specific type of nerve fiber being activated within one dorsal root P and i being a combination of dorsal roots P and neve fiber types that have been initialized and j being the current used;

Reiterate the selectivity index for a multitude of different lead L positions;

Find the minimal distance among all lead L positions;

Take the dist(j) function for that position for all possible active sites;

Minimize it through superposition of the active sites to calculate the multipolar configuration.

Alternatively, and/or additionally, the system 10 could optimize electrode E position and stimulation configuration for treatment of autonomic dysfunction.

FIG. 5 shows an example of neurofunctionalization with the system 10 disclosed in FIG. 1.

In this embodiment, the system 10 disclosed in FIG. 1 further comprises output device, cf. FIG. 2.

In this embodiment, the output device provide visual information on a display.

In other words, the shown embodiment is visual information provided by the output device.

In general, the output device could provide visualization of at least one of electric currents, potentials, information on the location and/or probability of the depolarization of nerve fibers and/or neurons.

In general, the output device could provide 3D visualization.

In this embodiment, the output device provides neurofunctionalization of a patient 3D FEM model M.

In this embodiment, spinal cord S, grey matter G, white matter W and dorsal roots R comprising myelinated axons AX (nerve fibers) are shown.

In this embodiment, simulations are performed using an electro-quasi-static solver.

In this embodiment, simulations of excitation after provided neuromodulation are performed.

In this embodiment, the simulations are coupled with electrophysiology models.

In this embodiment, the simulations are coupled with a nerve fiber-based electrophysiology model.

In this embodiment, a myelinated axon AX is shown in detail.

In this embodiment, a myelinated fiber AX (e.g. Aα-sensory fiber) with nodes of Ranvier N is shown. Nodes of Ranvier N are uninsulated and enriched in ion channels, allowing them to participate in the exchange of ions required to regenerate the action potential.

In this embodiment, the output device provide visualization of information on the location of the depolarization of a nerve fiber, in particular an axon AX after providing neuromodulation to the spinal cord S.

Finally, this embodiment illustrates some components of a compartmental cable model by showing the lumped elements used to model the ion-exchange at the nodes of Ranvier N.

In general, realistic compartmental cable models can automatically be created within the personalized 3D FEM models, including but not limited to, Aα-, Aβ-, Aδ-, C-sensory fibers, interneurons, α-motoneurons and efferent nerves, as well as dorsal column projections. In an alternative embodiment, the output device could provide visualization of information on the location and/or probability of the depolarization of nerve fibers and/or neurons.

In general, the system 10 could automatically determine the optimal stimulation parameters for recruiting a nerve fiber and/or neuron population with the spinal cord of a patient.

Figure 6:
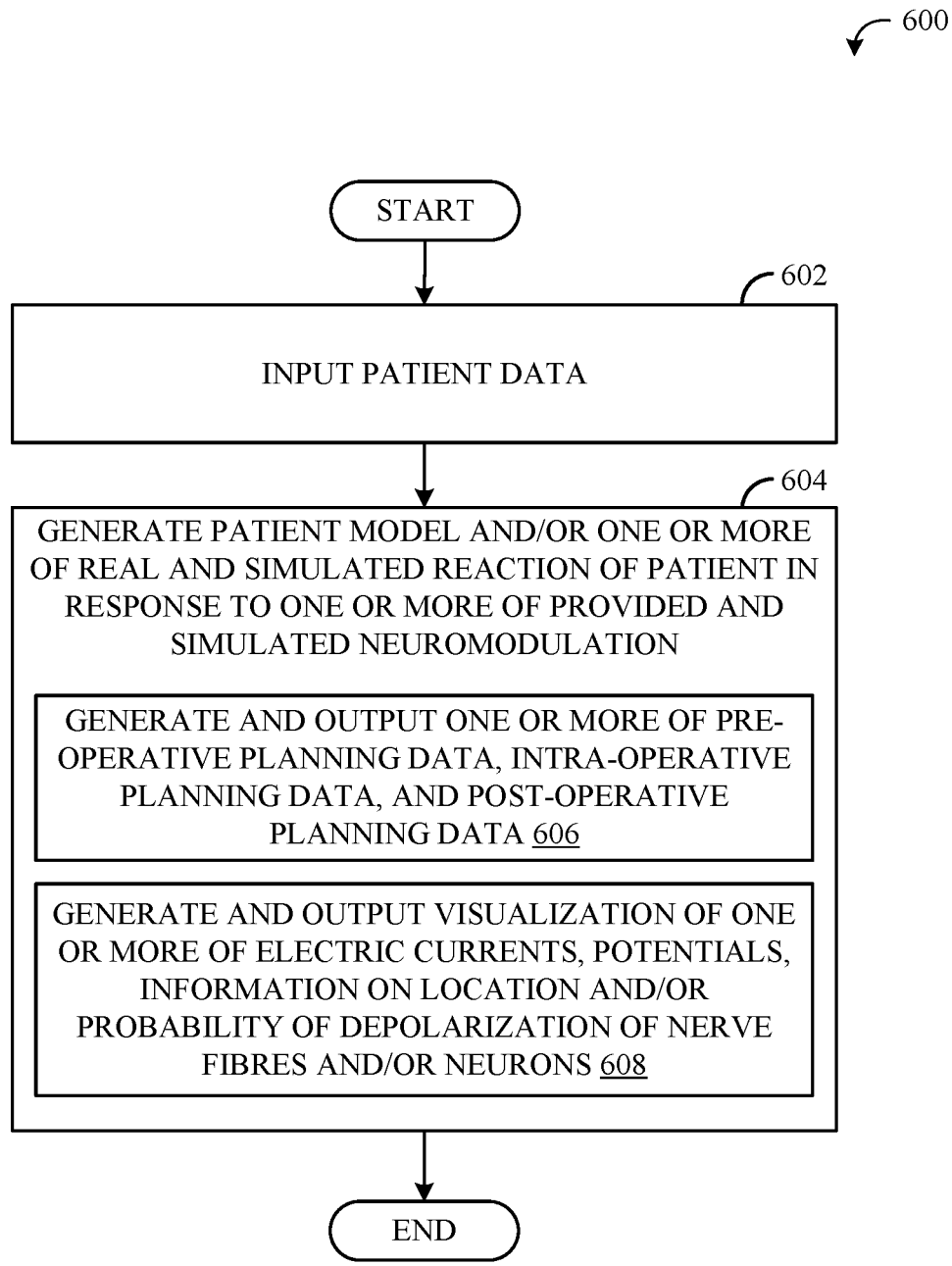
FIG. 6 shows a high level flow chart illustrating an example method for patient-specific neuromodulation.

Turning to FIG. 6, it shows a high-level flowchart illustrating an example method 600 for providing neuromodulation according to one or more of a patient's individual anatomy, need, and response. Method 600 is described with regard to systems, components, and methods of FIGS. 1-5, though it should be appreciated that method 600 may be implemented with other systems, components, and methods without departing from the scope of the present disclosure. Method 600 may be implemented as computer executable instruction in the memory 104 executed by the processor 106 of the device 102.

At 602, method 600 includes inputting patient data. Inputting patient data includes reading imaging datasets via an input module, such as input module 12, from a modality, such as modality 140. Example modalities that may be used to acquire the patient data may include MRI, CT, Fluoroimaging, X-Ray, IR, video, laser measuring, optical visualization and/or other imaging module, real-time registration, navigation system imaging, EEG, ECG, EMG, mechanical feedback and the like.

At 604, method 600 includes generating a patient model, such as patient model 250 and 306, and/or generating one or more of real reaction and simulated reaction of the patient in response to one or more of a provided neuromodulation and a simulated neuromodulation. The generation of the patient model and/or one or more of the real reaction and the simulated reaction may be performed via a model calculation and building module, such as model calculation and building module 14 at FIG. 1. Generating the patient model and/or generating one or more of real reaction and simulated reaction of the patient includes, at 606, generating and outputting (e.g., output via output device 124 of system 10 and/or a output device within system 10) one or more of pre-operative planning data, intra-operative planning data, and post-operative planning data. The pre-operative planning data may include at least one of surgical incision placement, optimal electrode placement, eligibility of the patient, in-silico assessment of benefit for decision making. The intra-operative planning data may include at least one intra-operative imaging data such as MRI, CT, Fluoroimaging, X-Ray, IR, video, laser measuring, optical visualization and imaging, real-time registration, navigation system imaging, EEG, ECG, EMG, mechanical feedback and the like. The post-operative planning data may include at least one recommended optimum electrode configuration, stimulation waveforms, timings schedule for neuromodulation events and the like. Further, at 606, one or more of electric currents, potentials, information on the location and/or probability of the depolarization of nerve fibers and/or neurons may be generated and output.

Those having skill in the art will appreciate that there are various logic implementations by which processes and/or systems described herein can be affected (e.g., hardware, software, and/or firmware), and that the preferred vehicle will vary with the context in which the processes are deployed. "Software" refers to logic that may be readily readapted to different purposes (e.g. read/write volatile or nonvolatile memory or media). "Firmware" refers to logic embodied as read-only memories and/or media. Hardware refers to logic embodied as analog and/or digital circuits. If an implementer determines that speed and accuracy are paramount, the implementer may opt for a hardware and/or firmware vehicle; alternatively, if flexibility is paramount, the implementer may opt for a solely software implementation; or, yet again alternatively, the implementer may opt for some combination of hardware, software, and/or firmware. Hence, there are several possible vehicles by which the processes described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood as notorious by those within the art that each function and/or operation within such block diagrams, flowcharts, or examples can be implemented, individually and/or collectively, by a wide range of hardware, software, firmware, or virtually any combination thereof. Several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in standard integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and/or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies equally regardless of the particular type of signal bearing media used to actually carry out the distribution. Examples of a signal bearing media include, but are not limited to, the following: recordable type media such as floppy disks, hard disk drives, CD ROMs, digital tape, flash drives, SD cards, solid state fixed or removable storage, and computer memory.

In a general sense, those skilled in the art will recognize that the various aspects described herein which can be implemented, individually and/or collectively, by a wide range of hardware, software, firmware, or any combination thereof can be viewed as being composed of various types of "circuitry." Consequently, as used herein "circuitry" includes, but is not limited to, electrical circuitry having at least one discrete electrical circuit, electrical circuitry having at least one integrated circuit, electrical circuitry having at least one Application specific integrated circuit, circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), circuitry forming a memory device (e.g., forms of random access memory), and/or circuits forming a communications device. (e.g., a modem, communications switch, or the like)

It will be appreciated that the configurations and routines disclosed herein are exemplary in nature, and that these specific embodiments are not to be considered in a limiting sense, because numerous variations are possible. The subject matter of the present disclosure includes all novel and non-obvious combinations and sub-combinations of the various systems and configurations, and other features, functions, and/or properties disclosed herein.

The following claims particularly point out certain combinations and sub-combinations regarded as novel and non-obvious. Such claims should be understood to include incorporation of one or more such elements, neither requiring nor excluding two or more such elements. Other combinations and sub-combinations of the disclosed features, functions, elements, and/or properties may be claimed through amendment of the present claims or through presentation of new claims in this or a related application. Such claims, whether broader, narrower, equal, or different in scope to the original claims, are also regarded as included within the subject matter of the present disclosure.

The invention claimed is:

1. A neuromodulation system comprising:
at least one input module for inputting patient data into the neuromodulation system;
at least one model calculation and building module for building a patient model, the patient model comprising three-dimensional reconstructions of dorsal roots of the patient, the three-dimensional reconstructions coupled with electrophysiology models of multiple types of nerve fibers included in the three-dimensional reconstructions of the dorsal roots; and
at least one computation module for calculating an impact of neuromodulation by determining a difference between a target and a simulated percentage activation of nerve fibers for multiple combinations of dorsal root and nerve fiber type using the three-dimensional reconstructions and the coupled electrophysiology models.

2. The neuromodulation system according to claim 1, wherein the system further comprises an output device for outputting at least one of pre-operative planning data, intra-operative planning data, or post-operative planning data.

3. The neuromodulation system according to claim 2, wherein the pre-operative planning data include at least one of surgical incision placement data, optimal electrode placement data, eligibility data of the patient, and assessment data of in silico benefit for decision making.

4. The neuromodulation system according to claim 2, wherein the intra-operative planning data include at least one intra-operative imaging data, the at least one intra-operative planning data including data acquired via a magnetic resonance imaging (MM), computed tomography (CT), Fluoroimaging, X-Ray, interventional radiology (IR), video, laser measuring, optical visualization and imaging system, real-time registration, navigation system imaging, electroencephalogram (EEG), electrocardiogram (ECG), electromyography (EMG), or mechanical feedback imaging systems.

5. The neuromodulation system according to claim 2, wherein the post-operative planning data include at least one of a recommended electrode configuration, electrode design, plan, stimulation waveforms, or timings schedule for neuromodulation events.

6. The neuromodulation system according to claim 2, wherein output device provides visualization of at least one of electric currents, potentials, information on location, or probability of depolarization of nerve fibers and/or neurons.

7. The system according to claim 1, wherein the patient data is acquired via a patient data acquisition modality communicatively coupled to the input module, the patient data acquisition modality including one of a MRI, a CT, a Fluoroimaging, an X-Ray, an IR, a video, a laser measuring, an optical visualization and imaging system, a real-time registration, a navigation system imaging, an EEG, an ECG, an EMG, or a mechanical feedback imaging system.

8. The system according to claim 1, wherein the at least one model calculation and building module or the at least one computation module is communicatively and operatively coupled to at least one of an implantable pulse generator or a spinal implant having a plurality of electrodes.

9. A method for providing neuromodulation, comprising at least the steps of:
inputting patient data of a patient;
building a patient model, the patient model comprising three-dimensional reconstructions of dorsal roots of the patient, the three-dimensional reconstructions coupled with electrophysiology models of multiple types of nerve fibers included in the three-dimensional reconstructions of the dorsal roots; and
calculating an impact of neuromodulation by determining a difference between a target and a simulated percentage activation of nerve fibers for multiple combinations of dorsal root and nerve fiber type using the three-dimensional reconstructions and the coupled electrophysiology models.

10. The method according to claim 9, further comprising a step of outputting at least one of pre-operative planning data, intra-operative planning data or post-operative planning data.

11. The method according to claim 10, wherein the pre-operative planning data includes at least one of surgical incision placement, optimal electrode placement, eligibility of the patient, or assessment in silico benefit for decision making.

12. The method according to claim 10, wherein, the intra-operative planning data includes at least one intra-operative imaging data, the at least one intra-operative imaging data acquired via a MRI, a CT, a Fluoroimaging, an X-Ray, an IR, a video, a laser measuring, an optical visualization and imaging system, a real-time registration, a navigation system imaging, an EEG, an ECG, an EMG, or a mechanical feedback imaging system.

13. The method according to claim 10 wherein the post-operative planning data includes at least one recommended electrode configuration, electrode design, plan, stimulation waveforms, or timings schedule for neuromodulation events.

14. The method according to claim 9, wherein the method further comprises outputting a visualization of at least one of electric currents; potentials; or information on:
locations of neurons or nerve fibers, or
probabilities of depolarization of neurons or nerve fibers.

15. The method according to claim 9, further comprising determining a desired placement of a lead comprising a plurality of electrodes according to the patient model.

16. The method according to claim 9, wherein the patient model further comprises a three-dimensional reconstruction of at least one of a spinal cord, a vertebral column, an epidural fat, a pia mater, a dura mater, a ventral root, cerebro-spinal fluid, white matter of the patient, or grey matter of the patient.

17. The method according to claim 9, wherein the patient model further includes a model of a lead, the lead including a plurality of electrodes.

18. The method according to claim 9, further comprising determining, according to the patient model, at least one of an electrode configuration or stimulation parameter for a nerve fiber or neuron population within a spinal cord of the patient.

19. The method according to claim 18, wherein the stimulation parameter includes frequency, amplitude, pulse width or polarity applied to a plurality of electrodes of a lead.

* * * * *